United States Patent
Van Wagenen et al.

(10) Patent No.: US 8,153,638 B2
(45) Date of Patent: *Apr. 10, 2012

(54) METABOTROPIC GLUTAMATE-RECEPTOR-POTENTIATING ISOINDOLONES

(75) Inventors: Bradford Van Wagenen, Salt Lake City, UT (US); Radhakrishnan Ukkiramapandian, Salt Lake City, UT (US); Joshua Clayton, Oakville (CA); Ian Egle, North York (CA); James R. Empfield, Wilmington, DE (US); Methvin Isaac, Brampton (CA); Fupeng Ma, Melrose, MA (US); Abdelmalik Slassi, Mississauga (CA); Gary Steelman, Wilmington, DE (US); Rebecca Urbanek, Wilmington, DE (US); Sally Walsh, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 6 days.

This patent is subject to a terminal disclaimer.

(21) Appl. No.: 12/861,336

(22) Filed: Aug. 23, 2010

(65) Prior Publication Data

US 2010/0317674 A1    Dec. 16, 2010

Related U.S. Application Data

(63) Continuation of application No. 12/063,007, filed on May 29, 2008, now Pat. No. 7,807,706.

(51) Int. Cl.
*A61K 31/497* (2006.01)
*A61K 31/4439* (2006.01)
*A61K 31/4035* (2006.01)
*A61K 31/427* (2006.01)
*C07D 403/14* (2006.01)
*C07D 403/02* (2006.01)
*C07D 401/02* (2006.01)
*C07D 209/44* (2006.01)
*C07D 417/02* (2006.01)

(52) U.S. Cl. .......... 514/255.05; 514/339; 514/416; 514/365; 544/405; 544/336; 546/277.1; 548/472; 548/181

(58) Field of Classification Search .......... 514/235.2, 514/253.09, 418; 544/144, 364; 548/486
See application file for complete search history.

(56) References Cited

U.S. PATENT DOCUMENTS

| | | | |
|---|---|---|---|
| 3,993,617 A | 11/1976 | Schwan | |
| 5,175,157 A | 12/1992 | Psiorz | |
| 5,681,954 A | 10/1997 | Yamamoto et al. | |
| 6,017,919 A | 1/2000 | Inaba et al. | |
| 7,799,792 B2 * | 9/2010 | Clayton et al. | 514/254.03 |
| 7,868,008 B2 * | 1/2011 | Van Wagenen et al. | 514/254.09 |
| 2003/0212094 A1 | 11/2003 | Yamabe et al. | |
| 2005/0026976 A1 | 2/2005 | Curtin et al. | |
| 2007/0082907 A1 * | 4/2007 | Canada et al. | 514/242 |
| 2008/0227794 A1 | 9/2008 | Van Wagenen et al. | |
| 2008/0306077 A1 * | 12/2008 | Clayton et al. | 514/249 |
| 2008/0306088 A1 | 12/2008 | Clayton et al. | |
| 2009/0111830 A1 * | 4/2009 | Wagenen et al. | 514/253.09 |
| 2009/0149505 A1 | 6/2009 | Empfield et al. | |
| 2009/0275578 A1 * | 11/2009 | Clayton et al. | 514/235.2 |

FOREIGN PATENT DOCUMENTS

| | | |
|---|---|---|
| BE | 620 654 A | 1/1963 |
| EP | 1528923 | 10/1978 |
| EP | 0548934 | 6/1993 |
| EP | 0602814 | 6/1994 |
| EP | 1431267 | 6/2004 |
| EP | 1726585 | 11/2006 |
| WO | 9217448 | 4/1991 |
| WO | 9854135 | 12/1998 |
| WO | 9926927 | 6/1999 |
| WO | 0210146 | 2/2002 |
| WO | 03101450 | 1/2003 |
| WO | 03087044 | 10/2003 |
| WO | 2004024702 | 3/2004 |
| WO | 2004031178 | 4/2004 |
| WO | 2004087048 | 10/2004 |
| WO | 2004089897 | 10/2004 |
| WO | 2005040157 | 5/2005 |
| WO | 2005074643 | 8/2005 |
| WO | 2005080397 | 9/2005 |

(Continued)

OTHER PUBLICATIONS

Orito Kazuhiko, et al; "Preparation of benzolactams by Pd(OAc)2-catalyzed direct aromatic carbonylation"; Journal of the American Chemical Society; Nov. 10, 2004; vol. 126, No. 44; pp. 14342-14343; ISSN: 0002-7863, Table 2, Compound 10B.

Tsuritani T, et al; "A short and efficient synthesis of isoindolin-1-ones"; Synlett, Mar. 17, 2006, Germany, No. 5, pp. 801-803, ISSN: 0936-5214, Table 2, Compound 7.

Morissette, et al. "High-throughput crystallization: polymorphs, salts, co-crystals and solvates of pharmaceutical solids". Advanced Drug Delivery Reviews 2004, 56, pp. 275-300.

(Continued)

*Primary Examiner* — Kamal Saeed
*Assistant Examiner* — Kristin Bianchi
(74) *Attorney, Agent, or Firm* — Kenneth F. Mitchell

(57) ABSTRACT

Compounds of formula I:

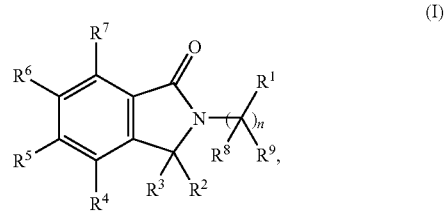

wherein $R^1$, $R^2$, $R^3$, $R^4$, $R^5$, $R^6$, $R^7$, $R^8$, $R^9$ and n are as defined in the description, processes for the preparing the compounds, new intermediates employed in the preparation, pharmaceutical compositions containing the compounds, and uses of the compounds in therapy.

3 Claims, No Drawings

FOREIGN PATENT DOCUMENTS

| WO | 2005085214 | 9/2005 |
|---|---|---|
| WO | 2005085216 | 9/2005 |
| WO | 2005100351 | 10/2005 |
| WO | 2006020879 | 2/2006 |
| WO | 2006047237 | 5/2006 |
| WO | 2006091496 | 8/2006 |
| WO | 2006123249 | 11/2006 |
| WO | 2006123255 | 11/2006 |
| WO | 2007000339 | 1/2007 |
| WO | 2007021308 | 2/2007 |
| WO | 2007021309 | 2/2007 |
| WO | 2007039439 | 4/2007 |
| WO | 2007095024 | 8/2007 |

OTHER PUBLICATIONS

Souillac, et al., Characterization of Delivery systems, Differential Scanning Calorimetry, pp. 217-218 (in Encyclopedia of Controlled Drug Delivery, 1999, John Wiley & Sons, pp. 212-227).

Vippagunta, Sudha R., "Crystalline Solids", Advanced Drug Delivery Reviews 48 (2001): 3-26.

Yamamoto, et al., "Synthesis of benzo-fused lactams . . . conjugated carbonyl groups", Org Biomol. Chem (2004); vol. 2, 1287-1294.

Moreau, et al, "A new approach to isoindoloisoquinolinones. A simple synthesis of neuvamine", Tetrahedron, vol. 60, No. 29, Jul. 12, 2004, pp. 6169-6176.

Anderson, et al., "Synthesis of 9,10-dihydroanthracen-9,10-imines", Journal of Organic Chemistry, vol. 44, No. 9, 1979, pp. 1519-1515.

Luzzio, et al, "A facile scheme for phthalimide—phthalimidine conversion", Tetrahedron Letters, vol. 40, No. 11, Mar. 12, 1999, pp. 2087-2090.

Hatt, et al, "Heterocyclic nitrogen compounds . . . in a Clemmensen reductionth", Journal of the Chemical Society, 1952, pp. 199-205.

Bohme, et al, "Untersuchungen in der Phthalimidin-Reihe", Die Pharmazie, No. 25, 1970 pp. 283-289.

Bailey, et al, "2,3-Diarylphthalimidines", Journal of Medicinal Chemistry, vol. 14, No. 3, pp. 240-241, 1971.

Mori, et al, "Reactions and syntheses with organometallic compounds. 7. Synthesis of benzolactams by palladium-catalyzed amidation", Journal of Organic Chemistry, vol. 43, No. 9, Apr. 28, 1978, pp. 1684-1687.

Grigg, et al, "Isoindolinones via a room temperature . . . carbonylation-amination cascade", Tetrahedron Letters, vol. 44, No. 37, Sep. 8, 2003, pp. 6979-6982.

Norman, et al, "Effect of linking bridge modifications on the antipsychotic profile of some phthalimide and isoindolinone derivatives", Journal of Medicinal Chemistry, vol. 39, No. 1, 1996, pp. 149-157.

Zhuang, et al, "Isoindol-1-one analogues . . . receptor ligands", Journal of Medicinal Chemistry, vol. 41, No. 2, Jan. 15, 1998, pp. 157-166.

Norman, et al, "Conformationally restricted analogues of remoxipride as potential antipsychotic agents" Journal of Medicinal Chemistry, vol. 36, No. 22, Oct. 29, 1993, pp. 3417-3423.

Ahn, et al, "N-Substituted-3-arylpyrrolidines: potent and selective ligands at serotonin 1A receptor", Bioorganic & Medicinal Chemistry Letters, vol. 9, No. 10, May 17, 1999, pp. 1379-1384.

Sugimoto, et al, "Synthesis and structure-activity . . . and related derivatives" Journal of Medicinal Chemistry, vol. 35, No. 24, 1992, pp. 4542-4548.

Mayer, et al, "New substituted . . . antagonist activity", Journal of Medicinal Chemistry, vol. 43, Sep. 19, 2000, pp. 3653-3664.

Breytenbach, et al, "Synthesis and antimicrobial activity of some isoindolin-1-ones derivatives", Bioorganic & Medicinal Chemistry Letters, vol. 10, No. 15, Aug. 7, 2000, pp. 1629-1631.

CA 139:133427 Synthetic communications 33(7), 1087-1094, 2003.

CA 133: 150436, Tetrahedron Letters, 41(20) 3891-3893, 2000.

CA 83:9678, Chemical & Pharmaceutical Bulletin, 23(1), pp. 184-187, 1975.

CA 79:105030, Roczniki Chemii, 47(5), pp. 937-942, 1973.

Eduardo E. Benarroch; "Metabotropic glutamate receptors: Synaptic modulators and therapeutic targets for neurologic disease", Neurology 2008; 70; pp. 964-968.

Sandeep T. Patil, et al; Activation of mGLu2/3 receptors as a new approach to treat schizophrenia: a randomized Phase 2 clinical trial; Nature Medicine vol. 13, No. 9, Sep. 2007; pp. 1102-1107.

Eric Mertz, et al, "Synthetic Receptors for CG Base Pairs", Organic Letters, 2000, vol. 2, No. 19, pp. 2931-2934.

Hyoung-Gon Lee, et al, "The Role of Metabotropic Glutamate Receptors in Alzheimer's Disease", Acta Neurobiol Exp 2004, 64(1): pp. 89-98.

Barr, et al; Journal of Organometallic Chemistry, vol. 302, No. 1, Mar. 11, 1986, pp. 117-126, XP002383544.

Hoarau C, et al; Synthesis No. 5, 2000, pp. 655-660, XP002383545.

Rys, V, et al; European Journal of Organic Chemistry, No. 7, Apr. 2003, pp. 1231-1237, XP002383546.

Clayden, j., et al; Organic Letters, vol. 2, No. 26, 2000, pp. 4229-4232 XP002345295.

Coulture, A., et al; Tetrahedron Letters, vol. 43, No. 12, Mar. 18, 2002, pp. 2207-2210 XP004344002.

Casagrande, C., et al; IL Farmaco, Edizione Scientifica, vol. 27, No. 6, Jun. 1972, pp. 445-470 XP000571647.

Bonnefous, et al., Bioorganic & Medicinal Chemistry Letters, vol. 15. pp. 4354-4358 (2005).

Bonnefous, et al. (Merck), poster presented at the 229th National Meeting of the American Chemical Society, San Diego, CA, Mar. 2005; Poster MEDI-37.

\* cited by examiner

METABOTROPIC GLUTAMATE-RECEPTOR-POTENTIATING ISOINDOLONES

CROSS REFERENCE TO RELATED APPLICATIONS

This application is a continuation of application Ser. No. 12/063,007 filed May 29, 2008 now U.S. Pat. No. 7,807,706 which claims the priority of P.C.T. Application PCT/US2005/028760, filed Aug. 12, 2005.

BACKGROUND OF THE INVENTION

The present invention relates to novel compounds that function as potentiators of glutamate receptors, methods for their preparation, pharmaceutical compositions containing them and their use in therapy.

The metabotropic glutamate receptors (mGluR) are a family of GTP-binding-protein (G-protein) coupled receptors that are activated by glutamate, and that have important roles in synaptic activity in the central nervous system, neural plasticity, neural development and neurodegeneration.

Activation of mGluRs in intact mammalian neurons elicits one or more of the following responses: activation of phospholipase C; increases in phosphoinositide (PI) hydrolysis; intracellular calcium release; activation of phospholipase D; activation or inhibition of adenyl cyclase; increases or decreases in the formation of cyclic adenosine monophosphate (cAMP); activation of guanylyl cyclase; increases in the formation of cyclic guanosine monophosphate (cGMP); activation of phospholipase $A_2$; increases in arachidonic acid release; and increases or decreases in the activity of voltage- and ligand-gated ion channels (Schoepp et al., 1993, Trends Pharmacol. Sci., 14:13; Schoepp, 1994, Neurochem. Int., 24:439; Pin et al., 1995, Neuropharmacology 34:1; Bordi & Ugolini, 1999, Prog. Neurobiol. 59:55).

Eight mGluR subtypes have been identified. The subtypes are divided into three groups based upon primary sequence similarity, signal transduction linkages, and pharmacological profile. Group-I includes mGluR1 and mGluR5, which activate phospholipase C and the generation of an intracellular calcium signal. Group-II (mGluR2 and mGluR3) and Group-III (mGluR4, mGluR6, mGluR7, and mGluR8) mGluRs mediate an inhibition of adenylyl cyclase activity and cyclic AMP levels. For a review, see Pin et al., 1999, Eur. J. Pharmacol., 375:277-294.

Activity of mGluR family receptors is implicated in a number of normal processes in the mammalian CNS, and are important targets for compounds for the treatment of a variety of neurological and psychiatric disorders. Activation of mGluRs is required for induction of hippocampal long-term potentiation and cerebellar long-term depression (Bashir et al., 1993, Nature, 363:347; Bortolotto et al., 1994, Nature, 368:740; Aiba et al., 1994, Cell, 79:365; Aiba et al., 1994, Cell, 79:377). A role for mGluR activation in nociception and analgesia also has been demonstrated (Meller et al., 1993, Neuroreport, 4: 879; Bordi & Ugolini, 1999, Brain Res., 871:223). In addition, mGluR activation has been suggested to play a modulatory role in a variety of other normal processes including synaptic transmission, neuronal development, apoptotic neuronal death, synaptic plasticity, spatial learning, olfactory memory, central control of cardiac activity, waking, motor control and control of the vestibulo-ocular reflex (Nakanishi, 1994, Neuron, 13:1031; Pin et al., 1995, Neuropharmacology, see above; Knopfel et al., 1995, J. Med. Chem., 38:1417).

Recent advances in the elucidation of the neurophysiological roles of mGluRs have established these receptors as promising drug targets in the therapy of acute and chronic neurological and psychiatric disorders and chronic and acute pain disorders. Because of the physiological and pathophysiological significance of the mGluRs, there is a need for new drugs and compounds that can modulate mGluR function.

SUMMARY OF THE INVENTION

We have identified a class of compounds that modulate mGluR function. In one aspect the invention provides compounds of formula I,

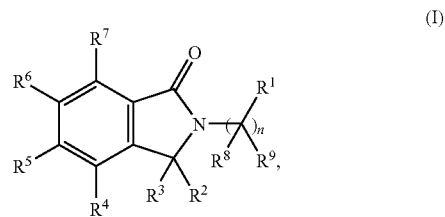

(I)

wherein:

$R^1$ is a 3- to 7-membered ring that may contain one or more heteroatoms independently selected from the group consisting of N, O and S, wherein said ring is substituted by one or more B;

$R^2$ and $R^3$ are independently selected from the group consisting of H, $C_{1-6}$-alkyl, $C_{2-6}$-alkenyl, $C_{2-6}$-alkynyl, aryl, heteroaryl, heterocycloalkyl, $C_{3-8}$-cycloalkyl, $C_{1-6}$-alkyl-aryl, $C_{1-6}$-alkyl-heteroaryl, $C_{1-6}$-alkyl-heterocycloalkyl, and $C_{1-6}$-alkyl-$C_{3-8}$-cycloalkyl, wherein $R^2$ and $R^3$ may be substituted by one or more A;

$R^4$ and $R^6$ are independently selected from the group consisting of H, hydroxy, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $(CO)R^{10}$, $O(CO)R^{10}$, $O(CO)OR^{10}$, $C(O)OR^{10}$, $O(CNR^{10})OR^{11}$, $C_{1-6}$-alkylOR$^{10}$, $OC_{2-6}$-alkylOR$^{10}$, $C_{1-6}$-alkyl(CO)R$^{10}$, $OC_{1-6}$-alkyl(CO)R$^{10}$, $OC_{0-6}$-alkylCO$_2$R$^{10}$, $OC_{1-6}$-alkylCO$_2$R$^{10}$, $C_{1-6}$-alkylcyano, $OC_{2-6}$-alkylcyano, $C_{0-6}$-alkylNR$^{10}$R$^{11}$, $OC_{2-6}$-alkylNR$^{10}$R$^{11}$, $C_{1-6}$-alkyl(CO)NR$^{10}$R$^{11}$, $OC_{1-6}$-alkyl(CO)NR$^{10}$R$^{11}$, $C_{0-6}$-alkylNR$^{10}$(CO)R$^{11}$, $OC_{2-6}$-alkylNR$^{10}$(CO)R$^{11}$, $C_{0-6}$-alkylNR$^{10}$(CO)NR$^{10}$R$^{11}$, $C_{0-6}$-alkylSR$^{10}$, $OC_{2-6}$-alkylSR$^{10}$, $C_{0-6}$-alkyl(SO)R$^{10}$, $OC_{2-6}$-alkyl(SO)R$^{10}$, $C_{0-6}$-alkylSO$_2$R$^{10}$, $OC_{2-6}$-alkylSO$_2$R$^{10}$, $C_{0-6}$-alkyl(SO$_2$)NR$^{10}$R$^{11}$, $OC_{2-6}$-alkyl(SO$_2$)NR$^{10}$R$^{11}$, $C_{0-6}$-alkylNR$^{10}$(SO$_2$)R$^{11}$, $OC_{2-6}$-alkylNR$^{10}$(SO$_2$)R$^{11}$, $C_{0-6}$-alkylNR$^{10}$(SO$_2$)NR$^{10}$R$^{11}$, $OC_{2-6}$-alkylNR$^{10}$(SO$_2$)NR$^{10}$R$^{11}$, $(CO)NR$^{10}$R$^{11}$, $O(CO)NR$^{10}$R$^{11}$, NR$^{10}$R$^{11}$, $C_{0-6}$-alkylNR$^{10}$(CO)OR$^{11}$, $OC_{2-6}$-alkyl NR$^{10}$(CO)OR$^{11}$, $SO_3R^{10}$ and a 5- to 7-membered ring that may contain one or more heteroatoms independently selected from the group consisting of N, O and S, wherein $R^4$ and $R^6$ may be substituted by one or more A, and wherein any cycloalkyl or aryl is optionally fused to a 5- to 7-membered ring that may contain one or more heteroatoms independently selected from the group consisting of C, N, O and S;

$R^5$ is selected from the group consisting of H, F, Cl, Br, I, nitro, CN, $C_{1-6}$-alkyl, $OC_{0-6}$-alkyl, $C_{1-6}$-alkylhalo, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $C_{1-6}$- alkylheteroaryl, $OC_{1-6}$-alkylaryl, $OC_{1-6}$-alkylheteroaryl, $C_{1-6}$-alkylheterocycloalkyl, Oheterocycloalkyl, $OC_{1-6}$-alkylheterocycloalkyl, C(O)H, $(CO)R^{10}$, $O(CO)R^{10}$, $O(CO)OR^{10}$, $C(O)OR^{10}$, $O(CN)OR^{10}$, $C_{1-6}$-alkyl$OR^{10}$, $OC_{2-6}$-alkyl$OR^{10}$, $C_{1-6}$-alkyl$(CO)R^{10}$, $OC_{1-6}$-alkyl$(CO)R^{10}$, $C_{0-6}$-alkyl$CO_2R^{10}$, $C_{1-6}$-alkylcyano, $OC_{2-6}$-alkylcyano, $C_{0-6}$-alkyl$OC_{2-6}$-alkyl$C_{1-6}$-alkyl$(CO)NR^{10}R^{11}$, $OC_{1-6}$-alkyl(CO)$NR^{10}R^{11}$, $C_{0-6}$-alkyl$NR^{10}(CO)R^{11}$, $OC_{2-6}$-alkyl$NR^{10}(CO)R^{11}$, $C_{0-6}$-alkyl$NR^{10}(CO)NR^{10}R^{11}$, $C_{0-6}$-alkyl$SR^{10}$, $OC_{2-6}$-alkyl$SR^{10}$, $C_{0-6}$-alkyl$(SO)R^{10}$, $OC_{2-6}$-alkyl$(SO)R^{10}$, $C_{0-6}$-alkyl$SO_2R^{10}$, $OC_{2-6}$-alkyl$SO_2R^{10}$, $C_{0-6}$-alkyl$(SO_2)NR^{10}R^{11}$, $OC_{2-6}$-alkyl$(SO_2)NR^{10}R^{11}$, $C_{0-6}$-alkyl$NR^{10}(SO_2)R^{11}$, $OC_{2-6}$-alkyl$NR^{10}(SO_2)R^{11}$, $C_{0-6}$-alkyl$NR^{10}(SO_2)NR^{10}R^{11}$, $OC_{2-6}$-alkyl$NR^{10}(SO_2)NR^{10}R^{11}$, $(CO)NR^{10}R^{11}$, $O(CO)NR^{10}R^{11}$, $NR^{10}R^{11}$, $C_{0-6}$-alkyl$NR^{10}(CO)OR^{11}$, $OC_{2-6}$-alkyl$NR^{10}(CO)OR^{11}$, $SO_3R^{10}$ and a 5- to 7-membered ring that may contain one or more heteroatoms independently selected from the group consisting of N, O and S, wherein $R^5$ may be substituted by one or more A, and wherein any cyclic moiety is optionally fused to a 5- to 7-membered ring that may contain one or more heteroatoms independently selected from the group consisting of C, N, O and S;

$R^7$ is selected from the group consisting of H, F, Cl, Br, I, nitro, cyano, $OC_{1-4}$-alkyl, $C_{1-6}$-alkyl, $C_{1-6}$-alkylhalo $OC_{1-6}$-alkylhalo $OC_{2-6}$-alkenyl, $OC_{2-6}$-alkenyl, $C_{2-6}$-alkynyl, $OC_{2-6}$-alkynyl, and $C_{3-8}$-cycloalkyl;

$R^8$ and $R^9$ are independently selected from the group consisting of H, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, and $OC_{2-6}$-alkynyl, or, where n is greater than 1, two or more $R^8$ and/or $R^9$ on adjacent carbon atoms may be absent to form an alkenyl or alkynyl moiety;

$R^{10}$ and $R^{11}$ are independently selected from the group consisting of H, hydroxy, oxo, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $C_{0-6}$-alkyl-heterocycloalkyl, $OC_{1-6}$-alkyl-heterocycloalkyl, heteroaryl, and $C_{1-6}$alkylheteroaryl, wherein any cyclic moiety is optionally fused to a 5- to 7-membered ring that may contain one or more heteroatoms independently selected from the group consisting of C, N, O and S and any cyclic moiety is optionally substituted with a substituent selected from alkyl, halo, hydroxyl, Oalkyl, haloalkyl and Ohaloalkyl;

A is selected from the group consisting of H, hydroxy, F, Cl, Br, I, nitro, cyano, oxo, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $C_{1-6}$-alkyl-heterocyclyl, $C_{1-6}$-alkyl-heterocycloalkyl, $OC_{0-6}$-alkyl-heterocycloalkyl, $(CO)R^{10}$, $O(CO)R^{10}$, $O(CO)OR^{10}$, $O(CNR^{10})OR^{11}$, $C_{1-6}$-alkyl$OR^{10}$, $OC_{2-6}$-alkyl$OR^{10}$, $C_{1-6}$-alkyl$(CO)R^{10}$, $OC_{1-6}$-alkyl$(CO)R^{10}$, $C_{0-6}$-alkyl$CO_2R^{10}$, $OC_{1-6}$-alkyl$CO_2R^{10}$, $C_{1-6}$-alkylcyano, $OC_{2-6}$-alkylcyano, $C_{0-6}$-alkyl$NR^{10}R^{11}$, $OC_{2-6}$-alkyl$NR^{10}R^{11}$, $C_{0-6}$-alkyl$(CO)NR^{10}R^{11}$, $OC_{1-6}$-alkyl$(CO)NR^{10}R^{11}$, $C_{0-6}$-alkyl$NR^{10}(CO)R^{11}$, $OC_{2-6}$-alkyl$NR^{10}(CO)R^{11}$, $C_{0-6}$-alkyl$NR^{10}(CO)NR^{10}R^{11}$, $C_{0-6}$-alkyl$SR^{10}$, $OC_{2-6}$-alkyl$SR^{10}$, $C_{0-6}$-alkyl$(SO)R^{10}$, $OC_{2-6}$-alkyl$(SO)R^{10}$, $C_{1-6}$-alkyl$SO_2R^{10}$, $OC_{2-6}$-alkyl$SO_2R^{10}$, $C_{0-6}$-alkyl$(SO_2)NR^{10}R^{11}$, $OC_{2-6}$-alkyl$(SO_2)NR^{10}R^{11}$, $C_{0-6}$-alkyl$NR^{10}(SO_2)R^{11}$, $OC_{2-6}$-alkyl$NR^{10}(SO_2)R^{11}$, $C_{0-6}$-alkyl$NR^{10}(SO_2)NR^{10}R^{11}$, $OC_{2-6}$-alkyl$NR^{10}(SO_2)NR^{10}R^{11}$, $(CO)NR^{10}R^{11}$, $O(CO)NR^{10}R^{11}$, $NR^{10}R^{11}$, $C_{0-6}$-alkyl$NR^{10}(CO)OR^{11}$, $OC_{2-6}$-alkyl$NR^{10}(CO)OR^{11}$, $SO_3R^{10}$ and a 5- to 7-membered ring that may contain one or more heteroatoms independently selected from the group consisting of N, O and S, wherein said 5- to 7-membered ring is optionally substituted by one or more of $R^{10}$ and $R^{11}$;

B is selected from the group consisting of $C_{3-8}$-cycloalkyl, $C_{1-6}$-alkyl-$C_{3-8}$-cycloalkyl, $OC_{0-6}$-alkyl-$C_{3-8}$-cycloalkyl, $C_{0-6}$-alkylaryl, $OC_{0-6}$-alkylaryl, $C_{1-6}$-alkyl-heterocycloalkyl, $C_{1-6}$-alkyl-heterocycloalkyl, $OC_{0-6}$-alkyl-heterocycloalkyl, $C_{0-6}$-alkyl-heteroaryl and $OC_{0-6}$-alkyl-heteroaryl, wherein any cyclic moiety is substituted with at least one substituent selected from the group consisting of halo, alkyl, alkylhalo, hydroxy, alkoxy, oxo, COR, $CO_2R$, $SO_2R$ and CN; and n is selected from the group consisting of 1, 2, 3, 4, 5, 6, 7, and 8;

or a pharmaceutically acceptable salt, hydrate, solvate, optical isomer, or combination thereof, with a proviso that said compound is not:

2-[4-(4-fluoro-phenoxy)-benzyl]-2,3-dihydro-isoindol-1-one;

2-[4-(4-trifluoromethyl-phenoxy)-benzyl]-2,3-dihydro-isoindol-1-one;

2-{3-[4-(4-fluoro-phenoxy)-phenyl]-propyl}-7-iodo-2,3-dihydro-isoindol-1-one, or 7-iodo-2-[3-(2-methoxy-phenoxy)-benzyl]-2,3-dihydro-isoindol-1-one.

The invention also provides processes for the preparation of compounds of formula I.

The invention further provides a pharmaceutical composition comprising a compound according to formula I together with a pharmaceutically acceptable carrier or excipient; in another aspect the invention provides a method for the treatment or prevention of neurological and psychiatric disorders associated with glutamate dysfunction in an animal in need of such treatment. The method comprises the step of administering to the animal a therapeutically effective amount of a compound of formula I or a pharmaceutical composition thereof.

The invention also provides for the use of a compound according to formula I, or a pharmaceutically acceptable salt or solvate thereof, in the manufacture of a medicament for the treatment of any of the conditions discussed herein. Further, the invention provides a compound of formula I, or a pharmaceutically acceptable salt or solvate thereof, for use in therapy.

DETAILED DESCRIPTION OF THE INVENTION

The present invention is based upon the discovery of compounds that exhibit activity as modulators of metabotropic glutamate receptors. More particularly, the compounds of the present invention exhibit activity as potentiators of the mGluR2 receptor, and are useful in therapy, in particular as pharmaceuticals for the treatment of neurological and psychiatric disorders associated with glutamate dysfunction.

The disclosure of P.C.T. Application PCT/US2005/028760 is incorporated herein by reference in its entirety.

DEFINITIONS

Unless specified otherwise within this specification, the nomenclature used in this specification generally follows the examples and rules stated in *Nomenclature of Organic Chemistry*, Sections A, B, C, D, E, F, and H, Pergamon Press, Oxford, 1979, which is incorporated by references herein for its exemplary chemical structure names and rules on naming chemical structures. Optionally, a name of a compound may be generated using a chemical naming program: ACD/Chem- Sketch, Version 5.09/September 2001, Advanced Chemistry Development, Inc., Toronto, Canada.

The term "alkyl" as used herein means a straight- or branched-chain hydrocarbon radical having, for example, from one to six carbon atoms, and includes methyl, ethyl, propyl, isopropyl, t-butyl and the like.

The term "alkenyl" as used herein means a straight- or branched-chain alkenyl radical having, for example, from two to six carbon atoms, and includes ethenyl, 1-propenyl, 1-butenyl and the like.

The term "alkynyl" as used herein means a straight- or branched-chain alkynyl radical having, for example, from two to six carbon atoms, and includes 1-propynyl (propargyl), 1-butyryl and the like.

The term "cycloalkyl" as used herein means a cyclic group (which may be unsaturated) having, for example, from three to seven carbon atoms, and includes cyclopropyl, cyclohexyl, cyclohexenyl and the like.

The term "heterocycloalkyl" as used herein means, for example, a three- to seven-membered cyclic group (which may be unsaturated) having at least one heteroatom selected from the group consisting of N, S and O, and includes piperidinyl, piperazinyl, pyrrolidinyl, tetrahydrofuranyl and the like.

The term "alkoxy" as used herein means a straight- or branched-chain alkoxy radical having, for example, from one to six carbon atoms and includes methoxy, ethoxy, propyloxy, isopropyloxy, t-butoxy and the like.

The term "halo" as used herein means halogen and includes fluoro, chloro, bromo, iodo and the like, in both radioactive and non-radioactive forms.

The term "aryl" as used herein means an aromatic group having, for example, five to twelve atoms, and includes phenyl, naphthyl and the like.

The term "heteroaryl" means an aromatic group which includes at least one heteroatom selected from the group consisting of N, S and O, and includes groups and includes pyridyl, indolyl, furyl, benzofuryl, thienyl, benzothienyl, quinolyl, oxazolyl and the like.

The term "alkanoyl" as used herein means a straight- or branched-chain alkanoyl radical having, for example, from two to seven atoms, and includes acetyl, propionyl, butyryl and the like.

The term "cycloalkenyl" as used herein means an unsaturated cylcoaklyl group having, for example, from four to seven carbon atoms, and includes cyclopent-1-enyl, cyclohex-1-enyl and the like.

The terms "alkylaryl", "alkylheteroaryl" and "alkylcycloalkyl" refer to an alkyl radical substituted with an aryl, heteroaryl or cycloalkyl group, and includes 2-phenethyl, 3-cyclohexyl propyl and the like.

The term "5- to 7-membered ring that may contain one or more heteroatoms independently selected from N, O and S" includes aromatic and heteroaromatic rings, as well as carbocyclic and heterocyclic rings which may be saturated or unsaturated, and includes furyl, isoxazolyl, oxazolyl, pyrazolyl, pyridazinyl, pyridyl, pyrimidyl, pyrrolyl, thiazolyl, thienyl, imidazolyl, triazolyl, morpholinyl, piperazinyl, piperidinyl, homopiperidinyl, tetrahydropyranyl, phenyl, cyclohexyl, cycloheptyl, cyclopentyl, cyclohexanyl and the like.

The term "pharmaceutically acceptable salt" means either an acid addition salt or a basic addition salt which is compatible with the treatment of patients.

A "pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms. The selection criteria for the appropriate salt will be known to one skilled in the art. Other non-pharmaceutically acceptable salts e.g. oxalates may be used for example in the isolation of compounds of Formula I for laboratory use, or for subsequent conversion to a pharmaceutically acceptable acid addition salt.

A "pharmaceutically acceptable basic addition salt" is any non-toxic organic or inorganic base addition salt of the acid compounds represented by Formula I or any of its intermediates. Illustrative inorganic bases which form suitable salts include lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

"Solvate" means a compound of Formula I or the pharmaceutically acceptable salt of a compound of Formula I wherein molecules of a suitable solvent are incorporated in a crystal lattice. A suitable solvent is physiologically tolerable at the dosage administered as the solvate. Examples of suitable solvents are ethanol, water and the like. When water is the solvent, the molecule is referred to as a hydrate.

The term "stereoisomers" is a general term for all isomers of the individual molecules that differ only in the orientation of their atoms in space. It includes mirror image isomers (enantiomers), geometric (cis/trans) isomers and isomers of compounds with more than one chiral centre that are not mirror images of one another (diastereomers).

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating the named disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

Compounds:

Compounds of the invention conform generally to formula I:

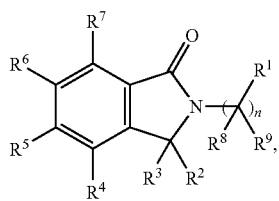

wherein:

$R^1$ is a 3- to 7-membered ring that may contain one or more heteroatoms independently selected from the group consisting of N, O and S, wherein said ring is substituted by one or more B;

$R^2$ and $R^3$ are independently selected from the group consisting of H, $C_{1-6}$-alkyl, $C_{2-6}$-alkenyl, $C_{2-6}$-alkynyl, aryl, heteroaryl, heterocycloalkyl, $C_{3-8}$-cycloalkyl, $C_{1-6}$-alkyl-aryl, $C_{1-6}$-alkyl-heteroaryl, $C_{1-6}$-alkyl-heterocycloalkyl, and $C_{1-6}$-alkyl-$C_{3-8}$-cycloalkyl, wherein $R^2$ and $R^3$ may be substituted by one or more A;

$R^4$ and $R^6$ are independently selected from the group consisting of H, hydroxy, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $(CO)R^{10}$, $O(CO)R^{10}$, $O(CO)OR^{10}$, $C(O)OR^{10}$, $O(CNR^{10})OR^{11}$, $C_{1-6}$-alkyl$OR^{10}$, $OC_{2-6}$-alkyl$OR^{10}$, $C_{1-6}$-alkyl$(CO)R^{10}$, $OC_{1-6}$-alkyl$(CO)R^{10}$, $C_{0-6}$-alkyl$CO_2R^{10}$, $OC_{1-6}$-alkyl$CO_2R^{10}$, $C_{1-6}$-alkylcyano, $OC_{2-6}$-alkylcyano, $C_{0-6}$-alkyl$NR^{10}R^{11}$, $OC_{2-6}$-alkyl$NR^{10}R^{11}$, $C_{1-6}$-alkyl$(CO)NR^{10}R^{11}$, $OC_{1-6}$-alkyl$(CO)NR^{10}R^{11}$, $C_{0-6}$-alkyl$NR^{10}(CO)R^{11}$, $OC_{2-6}$-alkyl$NR^{10}(CO)R^{11}$, $C_{0-6}$-alkyl$NR^{10}(CO)NR^{10}R^{11}$, $C_{0-6}$-alkyl$SR^{10}$, $OC_{2-6}$-alkyl$SR^{10}$, $C_{0-6}$-alkyl$(SO)R^{10}$, $OC_{2-6}$-alkyl$(SO)R^{10}$, $C_{0-6}$-alkyl$SO_2R^{10}$, $OC_{2-6}$-alkyl$SO_2R^{10}$, $C_{0-6}$-alkyl$(SO_2)NR^{10}R^{11}$, $OC_{2-6}$-alkyl$(SO_2)NR^{10}R^{11}$, $C_{0-6}$-alkyl$NR^{10}(SO_2)R^{11}$, $OC_{2-6}$-alkyl$NR^{10}(SO_2)R^{11}$, $C_{0-6}$-alkyl$NR^{10}(SO_2)NR^{10}R^{11}$, $OC_{2-6}$-alkyl$NR^{10}(SO_2)NR^{10}R^{11}$, $(CO)NR^{10}R^{11}$, $O(CO)NR^{10}R^{11}$, $NR^{10}R^{11}$, $C_{0-6}$-alkyl$NR^{10}(CO)OR^{11}$, $OC_{2-6}$-alkyl$NR^{10}(CO)OR^{11}$, $SO_3R^{10}$ and a 5- to 7-membered ring that may contain one or more heteroatoms independently selected from the group consisting of N, O and S, wherein $R^4$ and $R^6$ may be substituted by one or more A, and wherein any cycloalkyl or aryl is optionally fused to a 5- to 7-membered ring that may contain one or more heteroatoms independently selected from the group consisting of C, N, O and S;

$R^5$ is selected from the group consisting of H, F, Cl, Br, I, nitro, CN, $C_{1-6}$-alkyl, $OC_{0-6}$-alkyl, $C_{1-6}$-alkylhalo, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $C_{1-6}$-alkylheteroaryl, $OC_{1-6}$-alkylaryl, $OC_{1-6}$-alkylheteroaryl, $C_{1-6}$-alkylheterocycloalkyl, Oheterocycloalkyl, $OC_{1-6}$-alkyl-heterocycloalkyl, $C(O)H$, $(CO)R^{10}$, $O(CO)R^{10}$, $O(CO)OR^{10}$, $C(O)OR^{10}$, $O(CN)OR^{10}$, $C_{1-6}$-alkyl$OR^{10}$, $OC_{2-6}$-alkyl$OR^{10}$, $C_{1-6}$-alkyl$(CO)R^{10}$, $OC_{1-6}$-alkyl$(CO)R^{10}$, $C_{0-6}$-alkyl$CO_2R^{10}$, $C_{1-6}$-alkylcyano, $OC_{2-6}$-alkylcyano, $C_{0-6}$-alkyl$NR^{10}R^{11}$, $OC_{2-6}$-alkyl$NR^{10}R^{11}$, $C_{1-6}$-alkyl$(CO)$ $NR^{10}R^{11}$, $OC_{1-6}$-alkyl$(CO)NR^{10}R^{11}$, $C_{0-6}$-alkyl$NR^{10}(CO)R^{11}$, $OC_{2-6}$-alkyl$NR^{10}(CO)R^{11}$, $C_{0-6}$-alkyl$NR^{10}(CO)NR^{10}R^{11}$, $C_{0-6}$-alkyl$SR^{10}$, $OC_{2-6}$-alkyl$SR^{10}$, $C_{0-6}$-alkyl$(SO)$ $R^{10}$, $OC_{2-6}$-alkyl$(SO)R^{10}$, $C_{0-6}$-alkyl$SO_2R^{10}$, $OC_{2-6}$-alkyl$SO_2R^{10}$, $C_{0-6}$-alkyl$(SO_2)NR^{10}R^{11}$, $OC_{2-6}$-alkyl$(SO_2)NR^{10}R^{11}$, $C_{0-6}$-alkyl$NR^{10}(SO_2)R^{11}$, $OC_{2-6}$-alkyl$NR^{10}(SO_2)R^{11}$, $C_{0-6}$-alkyl$NR^{10}(SO_2)NR^{10}R^{11}$, $OC_{2-6}$-alkyl$NR^{10}(SO_2)NR^{10}R^{11}$, $(CO)NR^{10}R^{11}$, $O(CO)NR^{10}R^{11}$, $NR^{10}R^{11}$, $C_{0-6}$-alkyl$NR^{10}(CO)OR^{11}$, $OC_{2-6}$-alkyl$NR^{10}(CO)OR^{11}$, $SO_3R^{10}$ and a 5- to 7-membered ring that may contain one or more heteroatoms independently selected from the group consisting of N, O and S, wherein $R^5$ may be substituted by one or more A, and wherein any cyclic moiety is optionally fused to a 5- to 7-membered ring that may contain one or more heteroatoms independently selected from the group consisting of C, N, O and S;

$R^7$ is selected from the group consisting of H, F, Cl, Br, I, nitro, cyano, $OC_{1-4}$-alkyl, $C_{1-6}$-alkyl, $C_{1-6}$-alkylhalo, $OC_{1-6}$-alkylhalo, $C_{2-6}$-alkenyl, $OC_{2-6}$-alkenyl, $C_{2-6}$-alkynyl, $OC_{2-6}$-alkynyl, and $C_{3-8}$-cycloalkyl;

$R^8$ and $R^9$ are independently selected from the group consisting of H, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, and $OC_{2-6}$-alkynyl, or, where n is greater than 1, two or more $R^8$ and/or $R^9$ on adjacent carbon atoms may be absent to form an alkenyl or alkynyl moiety;

$R^{10}$ and $R^{11}$ are independently selected from the group consisting of H, hydroxy, oxo, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $C_{0-6}$-alkyl-heterocycloalkyl, $OC_{1-6}$-alkyl-heterocycloalkyl, heteroaryl, and $C_{1-6}$alkylheteroaryl, wherein any cyclic moiety is optionally fused to a 5- to 7-membered ring that may contain one or more heteroatoms independently selected from the group consisting of C, N, O and S and any cyclic moiety is optionally substituted with a substituent selected from alkyl, halo, hydroxyl, Oalkyl, haloalkyl and Ohaloalkyl;

A is selected from the group consisting of H, hydroxy, F, Cl, Br, I, nitro, cyano, oxo, $C_{1-6}$-alkyl, $C_{1-6}$-alkylhalo, $OC_{1-6}$ alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $C_{1-6}$-alkyl-heterocyclyl, $C_{1-6}$-alkyl-heterocycloalkyl, $OC_{0-6}$-alkyl-heterocycloalkyl, $(CO)R^{10}$, $O(CO)R^{10}$, $O(CO)OR^{10}$, $O(CNR^{10})OR^{11}$, $C_{1-6}$-alkyl$OR^{10}$, $OC_{2-6}$-alkyl$OR^{10}$, $C_{1-6}$-alkyl$(CO)R^{10}$, $OC_{1-6}$-alkyl$(CO)R^{10}$, $C_{0-6}$-alkyl$CO_2R^{10}$, $OC_{1-6}$-alkyl$CO_2R^{10}$, $C_{1-6}$-alkylcyano, $OC_{2-6}$-alkylcyano, $C_{0-6}$-alkyl$NR^{10}R^{11}$, $OC_{2-6}$-alkyl$NR^{10}R^{11}$, $C_{0-6}$-alkyl$(CO)NR^{10}R^{11}$, $OC_{1-6}$-alkyl$(CO)NR^{10}R^{11}$, $C_{0-6}$-alkyl$NR^{10}(CO)R^{11}$, $OC_{2-6}$-alkyl$NR^{10}(CO)R^{11}$, $C_{0-6}$-alkyl$NR^{10}(CO)NR^{10}R^{11}$, $C_{0-6}$-alkyl$SR^{10}$, $OC_{2-6}$-alkyl$SR^{10}$, $C_{0-6}$-alkyl$(SO)R^{10}$, $OC_{2-6}$-alkyl$(SO)R^{10}$, $C_{1-6}$-alkyl$SO_2R^{10}$, $OC_{2-6}$-alkyl$SO_2R^{10}$, $C_{0-6}$-alkyl$(SO_2)NR^{10}R^{11}$, $OC_{2-6}$-alkyl$(SO_2)NR^{10}R^{11}$, $C_{0-6}$-alkyl$NR^{10}(SO_2)R^{11}$, $OC_{2-6}$-alkyl$NR^{10}(SO_2)R^{11}$, $C_{0-6}$-alkyl$NR^{10}(SO_2)NR^{10}R^{11}$, $OC_{2-6}$-alkyl$NR^{10}(SO_2)NR^{10}R^{11}$, $(CO)NR^{10}R^{11}$, $O(CO)NR^{10}R^{11}$, $NR^{10}R^{11}$, $C_{0-6}$-alkyl$NR^{10}(CO)OR^{11}$, $OC_{2-6}$-alkyl$NR^{10}(CO)OR^{11}$, $SO_3R^{10}$ and a 5- to 7-membered ring that may contain one or more heteroatoms independently selected from the group consisting of N, O and S, wherein said 5- to 7-membered ring is optionally substituted by one or more of $R^{10}$ and $R^{11}$;

B is selected from the group consisting of $C_{3-8}$-cycloalkyl, $C_{1-6}$-alkyl-$C_{3-8}$-cycloalkyl, $OC_{0-6}$-alkyl-$C_{3-8}$-cycloalkyl, $C_{0-6}$-alkylaryl, $OC_{0-6}$-alkylaryl, $C_{1-6}$-alkyl-heterocycloalkyl, $C_{1-6}$-alkyl-heterocycloalkyl, $OC_{0-6}$-alkyl-heterocycloalkyl, $C_{0-6}$-alkyl-heteroaryl and $OC_{0-6}$-alkyl-heteroaryl, wherein any cyclic moiety is substituted with at least one substituent selected from the group consisting of halo, alkyl, alkylhalo, hydroxy, alkoxy, oxo, COR, $CO_2R$, $SO_2R$ and CN, and n is selected from the group consisting of 1, 2, 3, 4, 5, 6, 7, and 8;

or a pharmaceutically acceptable salt, hydrate, solvate, optical isomer, or combination thereof, with a proviso that said compound is not:

2-[4-(4-fluoro-phenoxy)-benzyl]-2,3-dihydro-isoindol-1-one;

2-[4-(4-trifluoromethyl-phenoxy)-benzyl]-2,3-dihydro-isoindol-1-one;

2-{3-[4-(4-fluoro-phenoxy)-phenyl]-propyl}-7-iodo-2,3-dihydro-isoindol-1-one, or 7-iodo-2-[3-(2-methoxy-phenoxy)-benzyl]-2,3-dihydro-isoindol-1-one.

Particular compounds according to Formula I, are those wherein:

$R^1$ is phenyl wherein said phenyl is substituted by one or more B;

$R^2$ and $R^3$ are independently selected from the group consisting of H, $C_{1-6}$-alkyl, $C_{2-6}$-alkenyl, $C_{2-6}$-alkynyl, aryl, heteroaryl, heterocycloalkyl, $C_{3-8}$-cycloalkyl, $C_{1-6}$-alkyl-aryl, $C_{1-6}$-alkyl-heteroaryl, $C_{1-6}$-alkyl-heterocycloalkyl, and $C_{1-6}$-alkyl-$C_{3-8}$-cycloalkyl, wherein $R^2$ and $R^3$ may be substituted by one or more A;

$R^4$ and $R^6$ are independently selected from the group consisting of H, hydroxy, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $(CO)R^{10}$, $O(CO)R^{10}$, $O(CO)OR^{10}$, $C(O)OR^{10}$, $O(CNR^{10})OR^{11}$, $C_{1-6}$-alkyl$OR^{10}$, $OC_{2-6}$-alkyl$OR^{10}$, $C_{1-6}$-alkyl$(CO)R^{10}$, $OC_{1-6}$-alkyl$(CO)R^{10}$, $C_{0-6}$-alkyl$CO_2R^{10}$, $OC_{1-6}$-alkyl$CO_2R^{10}$, $C_{1-6}$-alkylcyano, $OC_{2-6}$-alkylcyano, $C_{0-6}$-alkyl$NR^{10}R^{11}$, $OC_{2-6}$-alkyl$NR^{10}$, $C_{1-6}$-alkyl$(CO)NR^{10}R^{11}$, $OC_{1-6}$-alkyl$(CO)NR^{10}R^{11}$, $C_{0-6}$-alkyl$NR^{10}(CO)R^{11}$, $OC_{2-6}$-alkyl$NR^{10}(CO)R^{11}$, $C_{0-6}$-alkyl$NR^{10}(CO)NR^{10}R^{11}$, $C_{0-6}$alkyl$SR^{10}$$OC_{2-6}$-alkyl$SR^{10}$, $C_{0-6}$-alkyl$(SO)R^{10}$, $OC_{2-6}$-alkyl$(SO)R^{10}$, $C_{0-6}$-alkyl$SO_2R^{10}$, $OC_{2-6}$-alkyl$SO_2R^{10}$, $C_{0-6}$-alkyl$(SO_2)NR^{10}R^{11}$, $OC_{2-6}$-alkyl$(SO_2)NR^{10}R^{11}$, $C_{0-6}$-alkyl$NR^{10}(SO^2)R^{11}$, $OC_{2-6}$-alkyl$NR^{10}(SO_2)R^{11}$, $C_{0-6}$-alkyl$NR^{10}(SO_2)NR^{10}R^{11}$, $OC_{2-6}$-alkyl$NR^{10}(SO_2)NR^{10}R^{11}$, $(CO)NR^{10}R^{11}$, $O(CO)NR^{10}R^{11}$, $NR^{10}OR^{11}$, $C_{0-6}$-alkyl$NR^{10}(CO)OR^{11}$, $OC_{2-6}$-alkyl$NR^{10}(CO)OR^{11}$, $SO_3R^{10}$ and a 5- to 7-membered ring that may contain one or more heteroatoms independently selected from the group consisting of N, O and S, wherein $R^4$ and $R^6$ may be substituted by one or more A, and wherein any cycloalkyl or aryl is optionally fused to a 5- to 7-membered ring that may contain one or more heteroatoms independently selected from the group consisting of C, N, O and S;

$R^5$ is selected from the group consisting of H, F, Cl, Br, I, nitro, CN, $C_{1-6}$-alkyl, $OC_{0-6}$-alkyl, $C_{1-6}$-alkylhalo, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $C_{1-6}$-alkylheteroaryl, $OC_{1-6}$-alkylaryl, $OC_{1-6}$-alkylheteroaryl, $C_{1-6}$-alkylheterocycloalkyl, Oheterocycloalkyl, $OC_{1-6}$-alkyl-heterocycloalkyl, $C(O)H$, $(CO)R^{10}$, $O(CO)R^{10}$, $O(CO)OR^{10}$, $C(O)OR^{10}$, $O(CN)OR^{10}$, $C_{1-6}$-alkyl$OR^{10}$, $OC_{2-6}$-alkyl$OR^{10}$, $C_{1-6}$-alkyl$(CO)R^{10}$, $OC_{1-6}$-alkyl$(CO)R^{10}$, $C_{0-6}$-alkyl$CO_2R^{10}$, $C_{1-6}$-alkylcyano, $OC_{2-6}$-alkylcyano, $C_{0-6}$-alkyl$NR^{10}R^{11}$, $OC_{2-6}$-alkyl$NR^{10}R^{11}$, $C_{1-6}$-alkyl$(CO)NR^{10}R^{11}$, $OC_{1-6}$-alkyl$(CO)NR^{10}R^{11}$, $C_{0-6}$-alkyl$NR^{10}(CO)R^{11}$, $OC_{2-6}$-alkyl$NR^{10}(CO)R^{11}$, $C_{0-6}$-alkyl$NR^{10}(CO)NR^{10}R^{11}$, $C_{0-6}$-alkyl$SR^{10}$, $OC_{2-6}$-alkyl$SR^{10}$, $C_{0-6}$-alkyl$(SO)R^{10}$, $OC_{2-6}$-alkyl$(SO)R^{10}$, $C_{0-6}$-alkyl$SO_2R^{10}$, $OC_{2-6}$- alkyl$SO_2R^{10}$, $C_{0-6}$-alkyl$(SO_2)NR^{10}R^{11}$, $OC_{2-6}$-alkyl$(SO_2)$ $NR^{10}R^{11}$, $C_{0-6}$-alkyl$NR^{10}(SO_2)R^{11}$, $OC_{2-6}$-alkyl$NR^{10}(SO_2)$ $R^{11}$, $C_{0-6}$-alkyl$NR^{10}(SO_2)NR^{10}R^{11}$, $OC_{2-6}$-alkyl$NR^{10}(SO_2)$ $NR^{10}R^{11}$, $(CO)NR^{10}R^{11}$, $O(CO)NR^{10}R^{11}$, $NR^{10}R^{11}$, $C_{0-6}$-alkyl$NR^{10}(CO)OR^{11}$, $OC_{2-6}$-alkyl$NR^{10}(CO)OR^{11}$, $SO_3R^{10}$ and a 5- to 7-membered ring that may contain one or more heteroatoms independently selected from the group consisting of N, O and S, wherein $R^5$ may be substituted by one or more A, and wherein any cyclic moiety is optionally fused to a 5- to 7-membered ring that may contain one or more heteroatoms independently selected from the group consisting of C, N, O and S;

$R^7$ is selected from the group consisting of H, F, Cl, Br, I, nitro, cyano, $OC_{1-4}$-alkyl, $C_{1-6}$-alkyl, $C_{1-6}$-alkylhalo, $OC_{1-6}$-alkylhalo, $C_{2-6}$-alkenyl, $OC_{2-6}$-alkenyl, $C_{2-6}$-alkynyl, $OC_{2-6}$-alkynyl, and $C_{3-8}$-cycloalkyl;

$R^8$ and $R^9$ are both H;

$R^{10}$ and $R^{11}$ are independently selected from the group consisting of H, hydroxy, oxo, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $C_{0-6}$-alkyl-heterocycloalkyl, $OC_{1-6}$-alkyl-heterocycloalkyl, heteroaryl, and $C_{1-6}$alkylheteroaryl, wherein any cyclic moiety is optionally fused to a 5- to 7-membered ring that may contain one or more heteroatoms independently selected from the group consisting of C, N, O and S and any cyclic moiety is optionally substituted with a substituent selected from alkyl, halo, hydroxyl, Oalkyl, haloalkyl and Ohaloalkyl;

A is selected from the group consisting of H, hydroxy, F, Cl, Br, I, nitro, cyano, oxo, $C_{1-6}$-alkyl, $C_{1-6}$-alkylhalo, $OC_{1-6}$ alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $C_{1-6}$-alkyl-heterocyclyl, $C_{1-6}$-alkyl-heterocycloalkyl, $OC_{0-6}$-alkyl-heterocycloalkyl, $(CO)R^{10}$, $O(CO)R^{10}$, $O(CO)OR^{10}$, $O(CNR^{10})OR^{11}$, $C_{1-6}$-alkyl$OR^{10}$, $OC_{2-6}$-alkyl$OR^{10}$, $C_{1-6}$-alkyl$(CO)R^{10}$, $OC_{1-6}$-alkyl$(CO)R^{10}$, $C_{0-6}$-alkyl$CO_2R^{10}$, $OC_{1-6}$-alkyl$CO_2R^{10}$, $C_{1-6}$-alkylcyano, $OC_{2-6}$-alkylcyano, $C_{0-6}$-alkyl$NR^{10}R^{11}$, $OC_{2-6}$-alkyl$NR^{10}R^{11}$, $C_{0-6}$-alkyl$(CO)NR^{10}R^{11}$, $OC_{1-6}$-alkyl$(CO)NR^{10}R^{11}$, $C_{0-6}$-alkyl$NR^{10}(CO)R^{11}$, $OC_{2-6}$-alkyl$NR^{10}(CO)R^{11}$, $C_{0-6}$-alkyl$NR^{10}(CO)NR^{10}R^{11}$, $C_{0-6}$-alkyl$SR^{10}$, $OC_{2-6}$-alkyl$SR^{10}$, $C_{0-6}$-alkyl$(SO)R^{10}$, $OC_{2-6}$-alkyl$(SO)R^{10}$, $C_{1-6}$-alkyl$SO_2R^{10}$, $OC_{2-6}$-alkyl$SO_2R^{10}$, $C_{0-6}$-alkyl$(SO_2)NR^{10}R^{11}$, $OC_{2-6}$-alkyl$(SO_2)NR^{10}R^{11}$, $C_{0-6}$-alkyl$NR^{10}(SO_2)R^{11}$, $OC_{2-6}$-alkyl$NR^{10}(SO_2)R^{11}$, $C_{0-6}$-alkyl$NR^{10}(SO_2)NR^{10}R^{11}$, $OC_{2-6}$-alkyl$NR^{10}(SO_2)NR^{10}R^{11}$, $(CO)NR^{10}R^{11}$, $O(CO)NR^{10}R^{11}$, $NR^{10}R^{11}$, $C_{0-6}$-alkyl$NR^{10}(CO)OR^{11}$, $OC_{2-6}$-alkyl$NR^{10}(CO)OR^{11}$, $SO_3R^{10}$ and a 5- to 7-membered ring that may contain one or more heteroatoms independently selected from the group consisting of N, O and S, wherein said 5- to 7-membered ring is optionally substituted by one or more of $R^{10}$ and $R^{11}$;

B is selected from the group consisting of $C_{0-6}$-alkylaryl and $OC_{0-6}$-alkylaryl, wherein any aryl moiety is substituted with at least one substituent selected from the group consisting of halo, alkyl, alkylhalo, hydroxy, alkoxy, oxo, COR, $CO_2R$, $SO_2R$ and CN; and n is 1;

or a pharmaceutically acceptable salt, hydrate, solvate, optical isomer, or combination thereof.

Other particular compounds according to Formula I, are those wherein:

$R^1$ is phenyl wherein said phenyl is substituted by one or more B;

$R^2$ and $R^3$ are independently selected from the group consisting of H and $C_{1-6}$-alkyl;

$R^4$ is H and $R^6$ is selected from the group consisting of H, hydroxy, F, Cl, Br, I, nitro, cyano, $C_{1-6}$-alkyl, and $OC_{1-6}$alkyl;

$R^5$ is selected from the group consisting of H, F, Cl, Br, I, or a 5- to 7-membered ring that may contain one or more heteroatoms independently selected from the group consisting of N, O and S;

$R^7$ is selected from the group consisting of H or $C_{1-6}$-alkyl;

$R^8$ and $R^9$ are both H;

B is $OC_{0-6}$-alkylaryl, wherein said aryl moiety is substituted with at least one substituent selected from the group consisting of halo, alkyl, alkylhalo and alkoxy, and n is 1;

or a pharmaceutically acceptable salt, hydrate, solvate, optical isomer, or combination thereof.

Other compounds of the invention conform generally to formula I:

wherein $R^1$, $R^2$, $R^3$, $R^4$, $R^5$, $R^6$, $R^7$, $R^8$, $R^9$ and n are defined as hereinabove. In a particular embodiment, n is 1, 2, or 3. When n is greater than 1, two or more of $R^8$ and $R^9$ on adjacent carbon atoms can be missing so as to form partially or fully unsaturated moieties. Thus, for example, when n is 2 and two adjacent $R^8$ and $R^9$ are missing, the moiety is an alkenyl group. When four adjacent $R^8$ and $R^9$ are missing, the moiety is an alkynyl group. All of these combinations are contemplated. Most particularly, n is 1. In this context, $R^8$ and $R^9$ particularly are each H.

Another particular subset of compounds are those in which $R^4$ and $R^6$ in formula I are each H. Thus, the aromatic portion of the isoindolone core in this embodiment can be di-substituted at most.

In another embodiment, $R^1$ is a 5- to 7-membered ring that is selected from the group consisting of aryl, $C_{3-8}$-cycloalkyl, cycloalkenyl, and heterocyclyl optionally substituted by one or more A selected from the group consisting of F, Cl, Br, I, $OC_{1-6}$-alkylhalo, and $OC_{0-6}$-alkylaryl. Exemplary rings in this context include but are not limited to phenyl, naphthyl, $C_{3-8}$-cycloalkyl, cycloalkenyl, furanyl, tetrahydrofuranyl, thiophenyl, pyridyl, oxadiazolyl, quinolinyl, piperazinyl, and tetrahydropyranyl. Particularly, $R^1$ is phenyl optionally substituted by one or more A selected from the group consisting of F, Cl, Br, I, $OC_{1-6}$-alkylhalo, and $OC_{0-6}$-alkylaryl.

In another embodiment, $R^1$ is phenyl optionally substituted by one or more A selected from the group consisting of F, Cl, Br, I, $OC_{1-6}$-alkylhalo, and $OC_{0-6}$-alkylaryl. Additionally, $R^2$, $R^3$, $R^4$, $R^6$, $R^8$, and $R^9$ are each H and n is 1. Particular values for $R^7$ include H, Cl, Br, I, $C_{1-6}$-alkyl, and $OC_{1-4}$-alkyl, particularly H, Cl, Br, I, —$CH_3$, and —$OCH_3$, and most particularly Cl, Br, I, and —$OCH_3$.

In yet another embodiment, $R^1$ is a $C_{3-8}$-cycloalkyl group. Particularly, $R^1$ is cyclopropyl. In this embodiment, n is particularly 1, 2, or 3, and most particularly is 1.

Another particular subset of compounds are those in which $R^5$ is selected from the group consisting of $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{1-6}$-alkylaryl, and a 5- to 7-membered ring that may contain one or more heteroatoms independently selected from the group consisting of N, O and S. In this embodiment, $R^5$ may be substituted by one or more A, and any cycloalkyl or aryl is optionally fused to a 5- to 7-membered ring that may contain one or more heteroatoms independently selected from the group consisting of C, N, O and S. Particularly, $R^5$ is selected from $C_{1-6}$-alkylaryl and a 5- to 7-membered ring that may contain one or more heteroatoms independently selected from the group consisting of N, O and S, wherein $R^5$ may be substituted by one or more A. More particularly, $R^5$ is a 5- to 7-membered ring that may contain one or more heteroatoms independently selected from the group consisting of N, O and S, which ring is substituted by one or more A selected from the group consisting of $C_{1-6}$-alkyl-heterocyclyl and a 5- to 7-membered ring that may contain one or more heteroatoms independently selected from the group consisting of N, O and S.

In yet another embodiment, n is 1, 2, or 3; $R^4$, $R^6$, $R^8$ and $R^9$ are each H; $R^1$ is selected from the group consisting of aryl, $C_{3-8}$-cycloalkyl, cycloalkenyl, and heterocyclyl optionally substituted by one or more A selected from the group consisting of F, Cl, Br, I, $OC_{1-6}$-alkylhalo, and $OC_{0-6}$-alkylaryl; $R^7$ is selected from the group consisting of H, Cl, Br, I, $C_{1-6}$-alkyl, and $OC_{1-4}$-alkyl, and $R^5$ is selected from the group consisting of $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{1-6}$-alkylaryl, and a 5- to 7-membered ring that may contain one or more heteroatoms independently selected from the group consisting of N, O and S, wherein $R^5$ may be substituted by one or more A, and wherein any cyclic moiety is optionally fused to a 5- to 7-membered ring that may contain one or more heteroatoms independently selected from the group consisting of C, N, O and S.

In another embodiment, n is 1, 2, or 3; $R^4$, $R^6$, $R^8$ and $R^9$ are each H; $R^1$ is selected from phenyl, naphthyl, $C_{3-8}$-cycloalkyl, cycloalkenyl, furanyl, tetrahydrofuranyl, thiophenyl, pyridyl, oxadiazolyl, quinolinyl, piperazinyl, and tetrahydropyranyl optionally substituted by one or more A selected from the group consisting of F, Cl, Br, I, $OC_{1-6}$-alkylhalo, and $OC_{0-6}$-alkylaryl; $R^7$ is selected from Cl, Br, I, and —$OCH_3$, and $R^5$ is selected from $C_{1-6}$-alkylaryl and a 5- to 7-membered ring that may contain one or more heteroatoms independently selected from the group consisting of N, O and S, wherein $R^5$ may be substituted by one or more A.

In a still further embodiment, n is 1, 2, or 3; $R^4$, $R^6$, $R^8$ and $R^9$ are each H; $R^1$ is phenyl optionally substituted by one or more A selected from the group consisting of F, Cl, Br, I, $OC_{1-6}$-alkylhalo, and $OC_{0-6}$-alkylaryl; $R^7$ is selected from the group consisting of H, Cl, Br, I, $C_{1-6}$-alkyl, and $OC_{1-4}$-alkyl, and $R^5$ is a 5- to 7-membered ring that may contain one or more heteroatoms independently selected from the group consisting of N, O and S, wherein the 5- to 7-membered ring is substituted by one or more A selected from the group consisting of $C_{1-6}$-alkyl-heterocyclyl and a 5- to 7-membered ring that may contain one or more heteroatoms independently selected from the group consisting of N, O and S.

In another embodiment, n is 1; $R^2$, $R^3$, $R^4$, $R^6$, $R^8$ and $R^9$ are each H; $R^1$ is phenyl optionally substituted by one or more A selected from the group consisting of F, Cl, Br, I, $OC_{1-6}$-alkylhalo, and $OC_{0-6}$-alkylaryl; $R^7$ is selected from Cl, Br, I, and —$OCH_3$, and $R^5$ is selected from $C_{1-6}$-alkylaryl and a 5- to 7-membered ring that may contain one or more heteroatoms independently selected from the group consisting of N, O and S, wherein $R^5$ may be substituted by one or more A.

It will be understood by those of skill in the art that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of formula I. The optically active forms of the compound of the invention may be prepared, for example, by chiral chromatographic separation of a racemate, by synthesis from optically active starting materials or by asymmetric synthesis based on the procedures described thereafter.

It will also be appreciated by those of skill in the art that certain compounds of the present invention may exist as geometrical isomers, for example E and Z isomers of alkenes.

The present invention includes any geometrical isomer of a compound of formula I. It will further be understood that the present invention encompasses tautomers of the compounds of formula I.

It will also be understood by those of skill in the art that certain compounds of the present invention may exist in solvated, for example hydrated, as well as unsolvated forms. It will further be understood that the present invention encompasses all such solvated forms of the compounds of formula I.

Within the scope of the invention are also salts of the compounds of formula I. Generally, pharmaceutically acceptable salts of compounds of the present invention are obtained using standard procedures well known in the art, for example, by reacting a sufficiently basic compound, for example an alkyl amine with a suitable acid, for example, HCl or acetic acid, to afford a physiologically acceptable anion. It is also possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques.

In one embodiment of the present invention, the compound of formula I may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

Specific examples of the present invention include the compounds described herein, their pharmaceutically acceptable salts, hydrates, solvates and optical isomers thereof.

Pharmaceutical Compositions:

The compounds of the present invention may be formulated into conventional pharmaceutical composition comprising a compound of formula I, or a pharmaceutically acceptable salt or solvate thereof, in association with a pharmaceutically acceptable carrier or excipient. The pharmaceutically acceptable carriers can be either solid or liquid. Solid form preparations include, but are not limited to, powders, tablets, dispersible granules, capsules, cachets, and suppositories.

A solid carrier can be one or more substances, which may also act as diluents, flavoring agents, solubilizers, lubricants, suspending agents, binders, or table disintegrating agents. A solid carrier can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized moulds and allowed to cool and solidify.

Suitable carriers include, but are not limited to, magnesium carbonate, magnesium stearate, talc, lactose, sugar, pectin, dextrin, starch, tragacanth, methyl cellulose, sodium carboxymethyl cellulose, low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art. Exemplary compositions intended for oral use may contain one or more coloring, sweetening, flavoring and/or preservative agents.

Depending on the mode of administration, the pharmaceutical composition will include from about 0.05% w (percent by weight) to about 99% w, more particularly, from about 0.10% w to 50% w, of the compound of the invention, all percentages by weight being based on the total weight of the composition.

A therapeutically effective amount for the practice of the present invention can be determined by one of ordinary skill in the art using known criteria including the age, weight and response of the individual patient, and interpreted within the context of the disease which is being treated or which is being prevented.

Uses:

We have discovered that the compounds of the present invention exhibit activity as pharmaceuticals, in particular as modulators of metabotropic glutamate receptors. More particularly, the compounds of the present invention exhibit activity as potentiators of the mGluR2 receptor. Such compounds and pharmaceutical compositions containing them are therefore useful in therapy, in particular for the treatment of neurological and psychiatric disorders associated with glutamate dysfunction in an animal.

Neurological and psychiatric disorders amenable to treatment with compounds disclosed herein include, but are not limited to, disorders such as cerebral deficit subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's disease, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, cerebral deficits secondary to prolonged status epilepticus, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, social phobia, obsessive compulsive disorder, and post-traumatic stress disorder (PTSD)), mood disorders (including depression, mania, bipolar disorders), circadian rhythm disorders (including jet lag and shift work), trigeminal neuralgia, hearing loss, tinnitus, macular degeneration of the eye, emesis, brain edema, pain (including acute and chronic pain states, severe pain, intractable pain, neuropathic pain, inflammatory pain, and post-traumatic pain), tardive dyskinesia, sleep disorders (including narcolepsy), attention deficit/hyperactivity disorder, and conduct disorder.

The invention thus provides a use of any of the compounds according to formula I, or a pharmaceutically acceptable salt or solvate thereof, for the manufacture of a medicament for the treatment of any of the conditions discussed above.

Additionally, the invention provides a method for the treatment of a subject suffering from any of the conditions discussed above, whereby an effective amount of a compound according to formula I or a pharmaceutically acceptable salt or solvate thereof, is administered to a patient in need of such treatment. The invention also provides a compound of formula I or pharmaceutically acceptable salt or solvate thereof, as hereinbefore defined for use in therapy.

In the context of the present specification, the term "therapy" also includes "prophylaxis" unless there are specific indications to the contrary. The term "therapeutic" and "therapeutically" should be construed accordingly. The term "therapy" within the context of the present invention further encompasses the administration of an effective amount of a compound of the present invention, to mitigate either a pre-existing disease state, acute or chronic, or to mitigate a recurring condition. This definition also encompasses prophylactic therapies for prevention of recurring conditions and continued therapy for chronic disorders.

In use for therapy in a warm-blooded animal such as a human, the compounds of the present invention may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints. In particular embodiments of the invention, the route of administration is oral, intravenous, or intramuscular.

The dosage will depend on the route of administration, the severity of the disease, age and weight of the patient and other factors normally considered by the attending physician, who determines the individual regimen and dosage level for a particular patient.

As mentioned above, the compounds described herein may be provided or delivered in a form suitable for oral use, for example, in a tablet, lozenge, hard and soft capsule, aqueous solution, oily solution, emulsion, and suspension. Alternatively, the compounds may be formulated into a topical administration, for example, as a cream, ointment, gel, spray, or aqueous solution, oily solution, emulsion or suspension. The compounds described herein also may be provided in a form that is suitable for nasal administration, for example, as a nasal spray, nasal drops, or dry powder. The compounds can be administered to the vagina or rectum in the form of a suppository. The compounds described herein also may be administered parentally, for example, by intravenous, intravesicular, subcutaneous, or intramuscular injection or infusion. The compounds can be administered by insufflation (for example as a finely divided powder). The compounds may also be administered transdermally or sublingually.

In addition to their use in therapeutic medicine, the compounds of formula I, or salts thereof, are useful as pharmacological tools in the development and standardisation of in vitro and in vivo test systems for the evaluation of the effects of inhibitors of mGluR-related activity in laboratory animals as part of the search for new therapeutics agents. Such animals include, for example, cats, dogs, rabbits, monkeys, rats and mice.

Processes for Preparing:

The selection of a particular process to prepare a given compound is within the purview of the person of skill in the art. The choice of particular structural features and/or substituents may therefore influence the selection of one process over another.

Within these general guidelines, the following processes can be used to prepare exemplary subsets of compounds of this invention. Unless indicated otherwise, the variables described in the following schemes and processes have the same definitions as those given for formula I above.

In one process, for example, a compound of formula Ia:

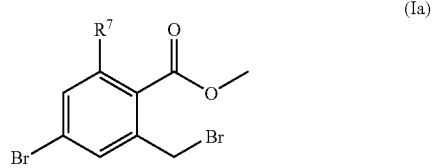

(Ia)

is cyclized in the presence of an amine of the formula $R^1(CR^8CR^9)_nNH_2$ to give a compound of formula Ib:

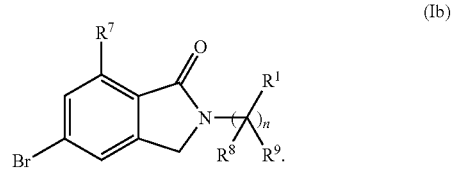

(Ib)

A compound of formula Ib is then cross-coupled with a suitable reagent containing $R^5$ to yield a compound according to formula Ic:

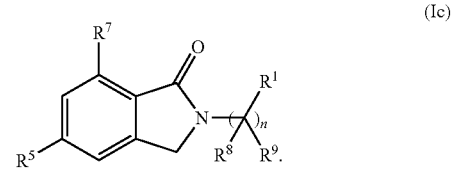

(Ic)

In one embodiment of this process, 5-substituted-7-methyl isoindolones are synthesized as depicted in Scheme 1 below. 4-bromo-2,6-dimethylaniline is converted to the corresponding nitrile under Sandmeyer reaction conditions. The nitrile is then hydrolyzed to the acid in a stepwise fashion. The amide can be obtained by basic hydrolysis. The amide is then diazotized and hydrolyzed with nitrososulphuric acid to provide the benzoic acid, which is subsequently protected as the methyl ester using standard conditions. The benzylic methyl group is monobrominated with N-bromosuccinimide using benzoyl peroxide as the radical initiator. This resultant intermediate is cyclized to the isoindolone with the appropriate amine in the presence of a base such as potassium carbonate. Finally, substituent $R^5$ was introduced at C5 of the isoindolone using typical Buchwald, Suzuki or Stille cross-coupling reaction conditions and reagents.

Scheme 1:

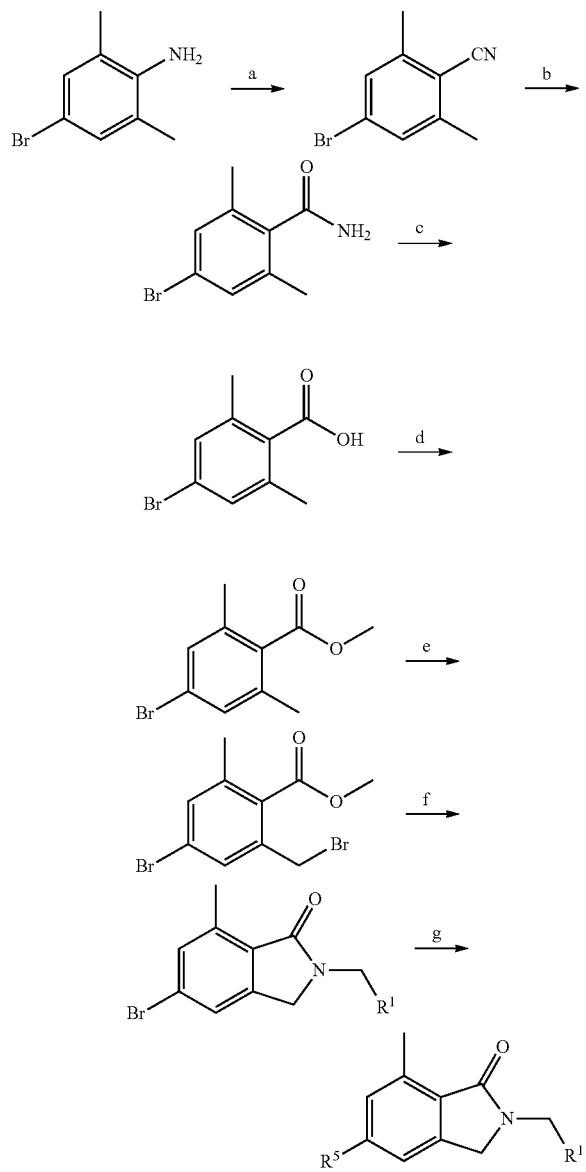

a NaCN, CuCN, HCl;
b NaOH;
c nitrososulphuric acid;
d MeI, K$_2$CO$_3$;
e NBS, (PhCO$_2$)$_2$;
f R1CH$_2$NH$_2$, K$_2$CO$_3$;
g R5H, BINAP, PdCl$_2$(dppf), NaOtBu OR R5B(OH)$_2$, PdCl$_2$(dppf), K$_2$CO$_3$ OR R5SnBu$_3$, Pd(PPh$_3$)$_4$ In another embodiment of this process, 5-substituted-7-chloro isoindolones are synthesized as depicted in Scheme 2 below. 4-bromo-2-methylbenzoic acid is chlorinated ortho to the acid using N-chlorosuccinimide and a palladium catalyst. In the manner analogous to that described above (Scheme 1), this acid was then esterified, brominated, and cyclized to yield the isoindolone intermediate. Substituent R$^5$ is introduced similarly.

Scheme 2:

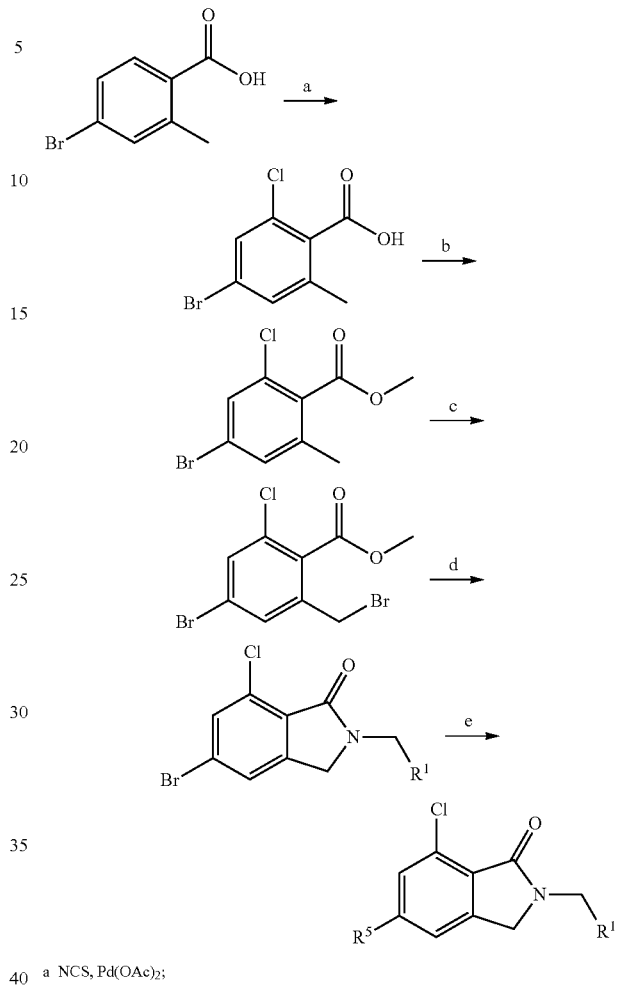

a NCS, Pd(OAc)$_2$;
b MeI, K$_2$CO$_3$;
c NBS, (PhCO$_2$)$_2$;
d R1CH$_2$NH$_2$, K$_2$CO$_3$;
e R5H, BINAP, PdCl$_2$(dppf), NaOtBu OR R5B(OH)$_2$, PdCl$_2$(dppf), K$_2$CO$_3$ OR R5SnBu$_3$, Pd(PPh$_3$)$_4$ In yet another embodiment of this process, isoindolones that are substituted with an amide at C5 can be prepared as depicted in Scheme 3 below. Thus, an appropriately substituted 5-bromoisoindolone is converted to the corresponding nitrile using zinc cyanide in the presence of a palladium catalyst. The nitrile is then hydrolyzed under basic conditions to provide the benzoic acid, which was then coupled with various amines using methodologies that are well-known in the art to provide the final compounds.

Scheme 3:

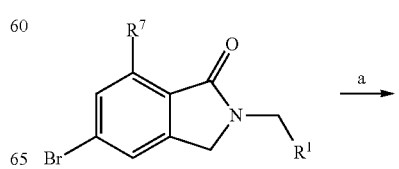

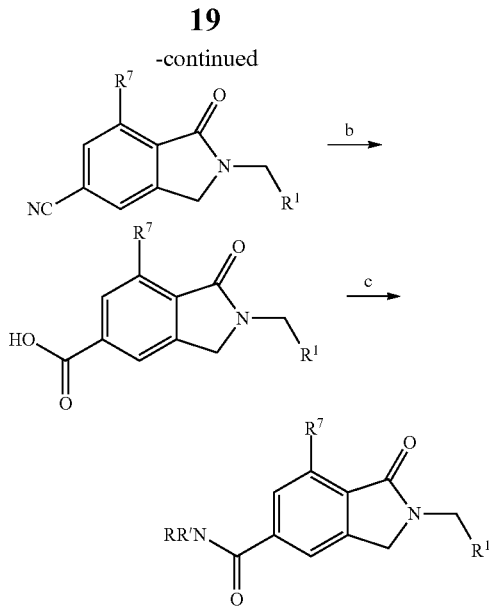

a Zn(CN)$_2$, Pd(PPh$_3$)$_4$;
b NaOH; (c) RR'NH, EDCl

Variations of the foregoing processes and additions thereto appear in the examples that follow. The person of ordinary skill in the art thus will appreciate that the compounds of this invention can be prepared by following or adapting one or more of the processes disclosed herein.

The invention is further illustrated by way of the following examples, which are intended to elaborate several embodiments of the invention. These examples are not intended to, nor are they to be construed to, limit the scope of the invention. It will be clear that the invention may be practiced otherwise than as particularly described herein. Numerous modifications and variations of the present invention are possible in view of the teachings herein and, therefore, are within the scope of the invention.

General Methods:

All starting materials are commercially available or earlier described in the literature.

$^1$H and $^{13}$C NMR spectra were recorded either on Bruker 300, Bruker DPX400 or Varian +400 spectrometers operating at 300, 400 and 400 MHz for $^1$H NMR respectively, using TMS or the residual solvent signal as reference, in deuterated chloroform as solvent unless otherwise indicated. All reported chemical shifts are in ppm on the delta-scale, and the fine splitting of the signals as appearing in the recordings (s: singlet, br s: broad singlet, d: doublet, t: triplet, q: quartet, m: multiplet).

Analytical in-line liquid chromatography separations followed by mass spectra detections, were recorded on a Waters LCMS consisting of an Alliance 2795 (LC) and a ZQ single quadropole mass spectrometer. The mass spectrometer was equipped with an electrospray ion source operated in a positive and/or negative ion mode. The ion spray voltage was ±3 kV and the mass spectrometer was scanned from m/z 100-700 at a scan time of 0.8 s. To the column, X-Terra MS, Waters, C8, 2.1×50 mm, 3.5 mm, was applied a linear gradient from 5% to 100% acetonitrile in10 mM ammonium acetate (aq.), or in 0.1% TFA (aq.).

Preparative reversed phase chromatography was run on a Gilson autopreparative HPLC with a diode array detector using an XTerra MS C8, 19×300 mm, 7 mm as column.

Purification by a chromatotron was performed on rotating silica gel/gypsum (Merck, 60 PF-254 with calcium sulphate) coated glass sheets, with coating layer of 1, 2, or 4 mm using a TC Research 7924T chromatotron.

Purification of products were also done using Chem Elut Extraction Columns (Varian, cat #1219-8002), Mega BE-SI (Bond Elut Silica) SPE Columns (Varian, cat #12256018; 12256026; 12256034), or by flash chromatography in silica-filled glass columns.

Microwave heating was performed in a Smith Synthesizer Single-mode microwave cavity producing continuous irradiation at 2450 MHz (Personal Chemistry AB, Uppsala, Sweden).

The pharmacological properties of the compounds of the invention can be analyzed using standard assays for functional activity. Examples of glutamate receptor assays are well known in the art as described in, for example, Aramori et al., 1992, Neuron, 8:757; Tanabe et al., 1992, Neuron, 8:169; Miller et al., 1995, J. Neuroscience, 15:6103; Balazs, et al., 1997, J. Neurochemistry, 1997, 69:151. The methodology described in these publications is incorporated herein by reference. Conveniently, the compounds of the invention can be studied by means of an assay that measures the mobilization of intracellular calcium, $[Ca^{2+}]_i$ in cells expressing mGluR2.

Fluorometric Imaging Plate Reader (FLIPR) analysis was used to detect allosteric activators of mGluR2 via calcium mobilization. A clonal HEK 293 cell line expressing a chimeric mGluR2/CaR construct comprising the extracellular and transmembrane domains of human mGluR2 and the intracellular domain of the human calcium receptor, fused to the promiscuous chimeric protein $G_{\alpha qi5}$ was used. Activation of this construct by agonists or allosteric activators resulted in stimulation of the PLC pathway and the subsequent mobilization of intracellular $Ca^{2+}$ which was measured via FLIPR analysis. At 24-hours prior to analysis, the cells were trypsinized and plated in DMEM at 100,000 cells/well in black sided, clear-bottom, collagen I coated, 96-well plates. The plates were incubated under 5% $CO_2$ at 37° C. overnight. Cells were loaded with 604 fluo-3 acetoxymethylester (Molecular Probes, Eugene Oreg.) for 60 minutes at room temperature. All assays were performed in a buffer containing 126 mM NaCl, 5 mM KCl, 1 mM $MgCl_2$, 1 mM $CaCl_2$, 20 mM Hepes, 0.06 μM DCG-IV (a Group II mGluR selective agonist), supplemented with 1.0 mg/ml D-glucose and 1.0 mg/ml BSA fraction IV (pH 7.4).

FLIPR experiments were done using a laser setting of 0.8 W and a 0.4 second CCD camera shutter speed. Extracellular fluo-3 was washed off and cells were maintained in 160 μL of buffer and placed in the FLIPR. An addition of test compound (0.01 μM to 30 μM in duplicate) was made after 10 seconds of baseline fluorescent readings were recorded on FLIPR. Fluorescent signals were then recorded for an additional 75 seconds at which point a second addition of DCG-IV (0.2 μM) was made and fluorescent signals were recorded for an additional 65 seconds. Fluorescent signals were measured as the peak height of the response within the sample period. Data was analyzed using Assay Explorer, and $EC_{50}$ and $E_{max}$ values (relative to maximum DCG-IV effect) were calculated using a four parameter logistic equation.

A [$^{35}$S]-GTPγS binding assay was used to functionally assay mGluR2 receptor activation. The allosteric activator activity of compounds at the human mGluR2 receptor were measured using a [$^{35}$S]-GTPγS binding assay with membranes prepared from CHO cells which stably express the human mGluR2. The assay is based upon the principle that agonists bind to G-protein coupled receptors to stimulate GDP-GTP exchange at the G-protein. Since [$^{35}$S]-GTPγS is a non-hydrolyzable GTP analog, it can be used to provide an index of GDP-GTP exchange and, thus, receptor activation.

The GTPγS binding assay therefore provides a quantitative measure of receptor activation.

Membranes were prepared from CHO cells stably transfected with human mGluR2. Membranes (30 μg protein) were incubated with test compound (3 nM to 300 μM) for 15 minutes at room temperature prior to the addition of 1 μM glutamate, and incubated for 30 min at 30° C. in 500 μL assay buffer (20 mM HEPES, 100 mM NaCl, 10 mM $MgCl_2$), containing 30 μM GDP and 0.1 nM [$^{35}$S]-GTPγS (1250 Ci/mmol). Reactions were carried out in triplicate in 2 mL polypropylene 96-well plates. Reactions were terminated by vacuum filtration using a Packard 96-well harvester and Unifilter-96, GF/B filter microplates. The filter plates were washed 4×1.5 mL with ice-cold wash buffer (10 mM sodium phosphate buffer, pH 7.4). The filter plates were dried and 35 μL of scintillation fluid (Microscint 20) was added to each well. The amount of radioactivity bound was determined by counting plates on the Packard TopCount. Data was analyzed using GraphPad Prism, and $EC_{50}$ and $E_{max}$ values (relative to the maximum glutamate effect) were calculated using non-linear regression.

Generally, the compounds of the present invention were active in assays described herein at concentrations (or with $EC_{50}$ values) less than 10 μM.

Exemplary Processes:

Compound 1: 2-[4-(4-Fluoro-phenoxy)-benzyl]-2,3-dihydro-isoindol-1-one

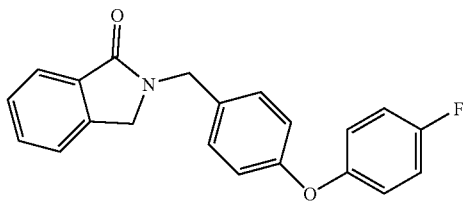

A mixture of 2-bromomethyl-benzoic acid methyl ester (0.108 g, 0.5 mmol), 4-(4-fluoro-phenoxy)-benzylamine (0.115 g, 0.5 mmol), and $K_2CO_3$ (0.235 g, 1.7 mmol) in toluene (5 mL) was heated with stirring at 100° C. for 2 h. Workup and silica gel column chromatography using 30% ethyl acetate in hexane afforded 2-[4-(4-fluoro-phenoxy)-benzyl]-2,3-dihydro-isoindol-1-one (0.100 g, 60%). $^1$H NMR (300 MHz, $CDCl_3$): δ (ppm) 4.29 (s, 2H), 4.78 (s, 2H) 6.83-7.56 (m, 11H), 7.89 (d, 1H). GC-MS: m/z 333 (M)'.

Compound 2: 2-[4-(4-Trifluoromethyl-phenoxy)-benzyl]-2,3-dihydro-isoindol-1-one

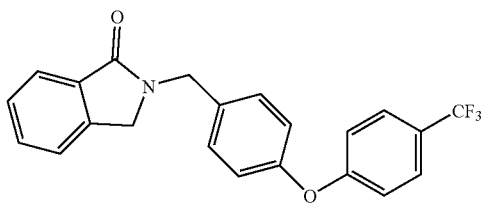

A mixture of 2-bromomethyl-benzoic acid methyl ester (0.115 g, 0.5 mmol), 4-(4-trifluoromethyl-phenoxy)-benzylamine (0.133 g, 0.5 mmol), and $K_2CO_3$ (0.235 g, 1.7 mmol) in toluene (5 mL) was heated with stirring at 100° C. for 2 h. Workup and silica gel column chromatography using 30% ethyl acetate in hexane afforded 2-[4-(4-trifluoromethyl-phenoxy)-benzyl]-2,3-dihydro-isoindol-1-one (0.116 g, 60%). $^1$H NMR (300 MHz, $CDCl_3$): δ (ppm) 4.32 (s, 2H), 4.81 (s, 2H) 7.01-7.56 (m, 11H), 7.91 (d, 1H). GC-MS: m/z 383 (M)$^+$.

Compound 3: -{3-[4-(4-Fluoro-phenoxy)-phenyl]-propyl}-7-iodo-2,3-dihydro-isoindol-1-one

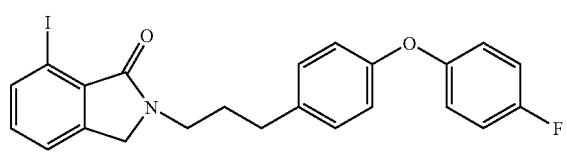

A mixture of 2-bromomethyl-6-iodo-benzoic acid methyl ester (0.245 g, 0.7 mmol), 3-[4-(4-fluoro-phenoxy)phenyl]-propylamine (0.193 g, 0.8 mmol), and $K_2CO_3$ (0.207 g, 1.5 mmol) in toluene (5 mL) was heated with stirring at 100° C. for 2 h. Workup and silica gel column chromatography using 30% ethyl acetate in hexane afforded 2-{3-[4-(4-fluoro-phenoxy)-phenyl]-propyl}-7-iodo-2,3-dihydro-isoindol-1-one (0.086 g, 25%). $^1$H NMR (300 MHz, $CDCl_3$): δ (ppm) 2.01 (m, 2H), 2.65 (t, 2H), 3.67 (t, 2H), 4.26 (s, 2H), 6.84-7.42 (m, 10H), 7.90 (d, 1H). GC-MS: m/z 487 (M)$^+$.

Compound 4: 7-Iodo-2-[3-(2-methoxy-phenoxy)-benzyl]-2,3-dihydro-isoindol-1-one

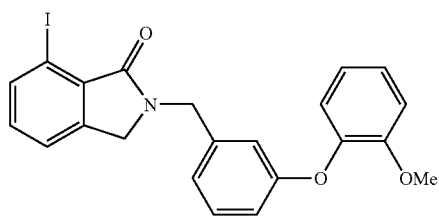

A mixture of 2-bromomethyl-6-iodo-benzoic acid methyl ester (0.178 g, 0.5 mmol), 3-(2-methoxy-phenoxy)-benzylamine (0.160 g, 0.6 mmol), and $K_2CO_3$ (0.138 g, 1.0 mmol) in toluene (5 mL) was heated with stirring at 100° C. for 2 h. Workup and silica gel column chromatography using 30% ethyl acetate in hexane afforded 7-iodo-2-[3-(2-methoxy-phenoxy)-benzyl]-2,3-dihydro-isoindol-1-one (0.056 g, 24%). $^1$H NMR (300 MHz, $CDCl_3$): δ (ppm) 3.82 (s, 3H), 4.16 (s, 2H), 4.74 (s, 2H), 6.84-7.40 (m, 10H), 7.92 (d, 1H). GC-MS: m/z 471 (M)$^+$.

The following Examples were prepared by processes analogous to those described in Compounds 1, 2, 3 and 4:

EXAMPLE 1

5-Bromo-2-[4-(2-fluorophenoxy)benzyl]-7-methyl-2,3-dihydro-isoindol-1-one

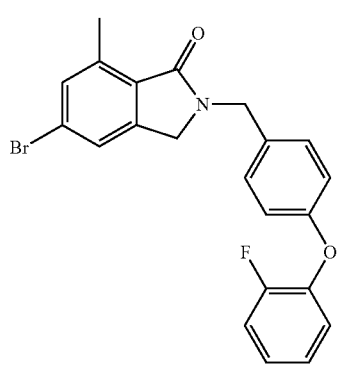

0.80 g, 42%, yellow oil. 7.37 (d, 2H), 7.27 (d, 2H), 7.02-7.22 (m, 4H), 6.95 (d, 2H), 4.73 (s, 2H), 4.21 (s, 2H), 2.74 (s, 3H).

EXAMPLE 2

5-Bromo-2-[4-(3-fluorophenoxy)benzyl]-7-methyl-2,3-dihydro-isoindol-1-one

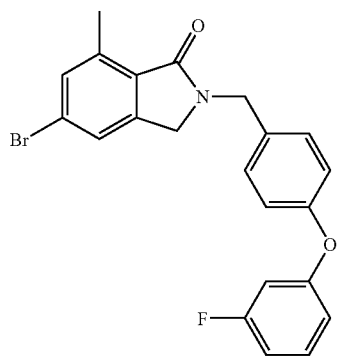

0.58 g, 26%, yellow solid. 7.38 (d, 2H), 7.27-7.33 (m, 3H), 7.02 (d, 2H), 6.75-6.85 (m, 2H), 6.66-6.72 (m, 1H), 4.76 (s, 2H), 4.24 (s, 2H), 2.75 (s, 3H).

EXAMPLE 3

5-Bromo-2-[4-(4-fluorophenoxy)benzyl]-7-methyl-2,3-dihydro-isoindol-1-one

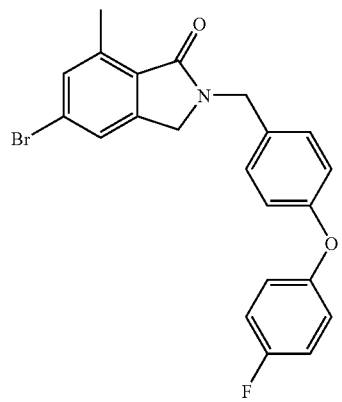

0.38 g, 34%, yellow oil. 7.37 (d, 2H), 7.27 (d, 2H), 6.90-7.10 (m, 6H), 4.73 (s, 2H), 4.22 (s, 2H), 2.75 (s, 3H).

EXAMPLE 4

5-Bromo-7-methyl-2-[4-(pyridin-2-yloxy)benzyl]-2,3-dihydro-isoindol-1-one

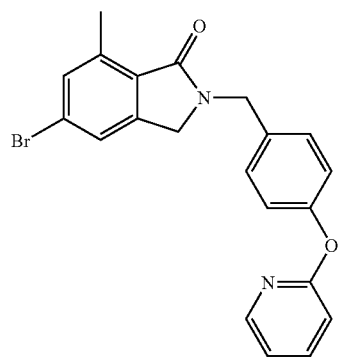

0.42 g, 40%, yellow oil. 8.17-8.22 (m, 1H), 7.67-7.75 (m, 1H), 7.33-7.39 (m, 4H), 7.13 (d, 2H), 7.00-7.05 (m, 1H), 6.93 (d, 2H), 4.77 (s, 2H), 4.25 (s, 2H), 2.75 (s, 3H).

EXAMPLE 5

5-Bromo-7-methyl-2-[4-(pyridin-3-yloxy)benzyl]-2,3-dihydro-isoindol-1-one

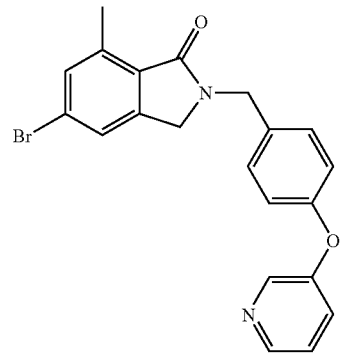

0.19 g, 9%, orange solid. 8.37-8.42 (m, 2H), 7.38 (d, 2H), 7.28-7.33 (m, 4H), 7.01 (d, 2H), 4.76 (s, 2H), 4.24 (s, 2H), 2.75 (s, 3H).

EXAMPLE 6

2-[4-(2-Fluoro-phenoxy)-benzyl]-7-methyl-5-pyridin-2-yl-2,3-dihydro-isoindol-1-one

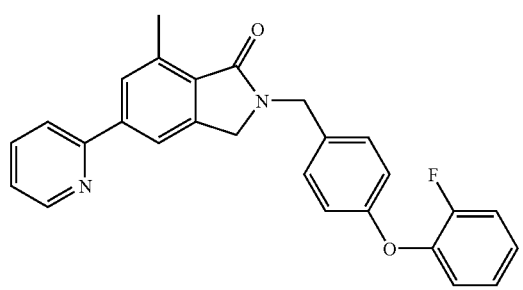

64 mg, 64%, pale yellow solid. 8.70-8.75 (m, 1H), 7.77-7.85 (m, 4H), 7.27-7.32 (m, 3H), 7.02-7.23 (m, 4H), 6.97 (d, 2H), 4.79 (s, 2H), 4.31 (s, 2H), 2.85 (s, 3H).

EXAMPLE 7

2-[4-(2-Fluoro-phenoxy)-benzyl]-7-methyl-5-pyridin-3-yl-2,3-dihydro-isoindol-1-one

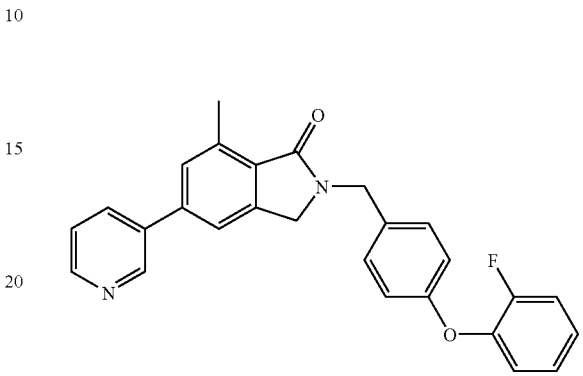

38 mg, 38%, pale yellow oil. 8.86 (d, 1H), 8.65 (dd, 1H), 7.85-7.92 (m, 1H), 7.38-7.41 (m, 3H), 7.30 (d, 2H), 7.02-7.23 (m, 4H), 6.96 (d, 2H), 4.79 (s, 2H), 4.32 (s, 2H), 2.85 (s, 3H).

EXAMPLE 8

2-[4-(2-Fluoro-phenoxy)-benzyl]-7-methyl-5-pyrazin-2-yl-2,3-dihydro-isoindol-1-one

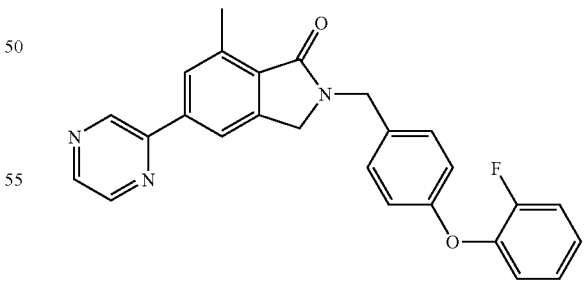

24 mg, 24%, off-white solid. 9.07 (d, 1H), 8.68 (dd, 1H), 8.58 (d, 1H), 7.87 (s, 2H), 7.29 (d, 2H), 7.02-7.23 (m, 4H), 6.96 (d, 2H), 4.79 (s, 2H), 4.34 (s, 2H), 2.87 (s, 3H).

EXAMPLE 9

7-Methyl-5-pyrazin-2-yl-2-[4-(pyridin-2-yloxy)-benzyl]-2,3-dihydro-isoindol-1-one

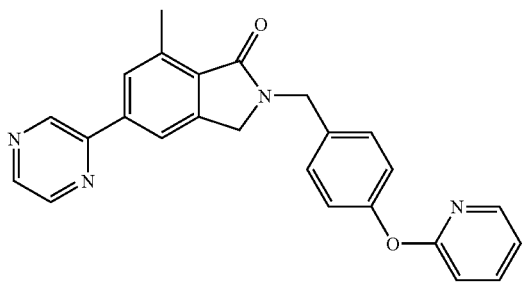

22 mg, 22%, off-white solid. 9.08 (d, 1H), 8.67-8.69 (m, 1H), 8.58 (d, 1H), 8.15-8.25 (m, 1H), 7.87 (s, 2H), 7.65-7.75 (m, 1H), 7.39 (d, 2H), 7.14 (d, 2H), 6.98-7.05 (m, 1H), 6.93 (d, 1H), 4.83 (s, 2H), 4.38 (s, 2H), 2.88 (s, 3H).

EXAMPLE 10

2-[4-(4-Fluoro-phenoxy)-benzyl]-7-methyl-5-pyridin-2-yl-2,3-dihydro-isoindol-1-one

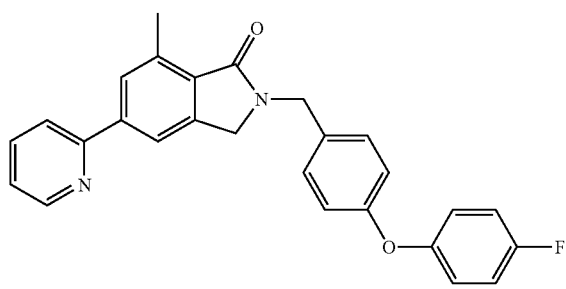

43 mg, 51%, yellow oil. 8.72-8.74 (m, 1H), 7.77-7.86 (m, 4H), 7.28-7.32 (m, 3H), 6.80-7.04 (m, 6H), 4.78 (s, 2H), 4.32 (s, 2H), 2.86 (s, 3H).

EXAMPLE 11

2-[4-(4-Fluoro-phenoxy)-benzyl]-7-methyl-5-pyridin-3-yl-2,3-dihydro-isoindol-1-one

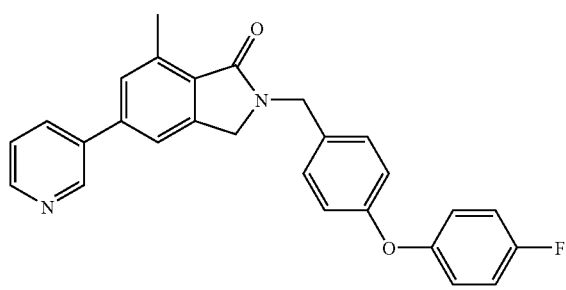

22 mg, 25%, yellow oil. 8.86 (d, 1H), 8.63-8.66 (m, 1H), 7.85-7.95 (m, 1H), 7.40-7.43 (m, 3H), 7.30 (d, 2H), 6.90-7.05 (m, 6H), 4.79 (s, 2H), 4.33 (s, 2H), 2.85 (s, 3H).

EXAMPLE 12

2-[4-(4-Fluoro-phenoxy)-benzyl]-7-methyl-5-pyrazin-2-yl-2,3-dihydro-isoindol-1-one

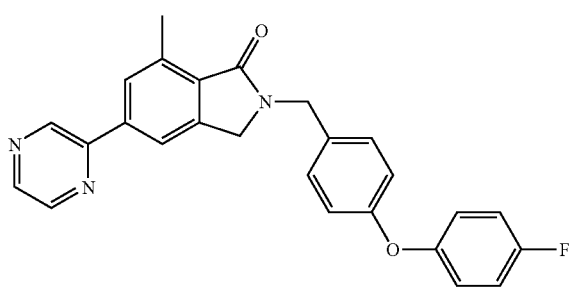

21 mg, 25%, pale yellow solid. 9.07 (d, 1H), 8.67-8.69 (m, 1H), 8.58 (d, 1H), 7.87 (s, 2H), 7.31 (d, 2H), 6.90-7.08 (m, 6H), 4.79 (s, 2H), 4.34 (s, 2H), 2.87 (s, 3H).

EXAMPLE 13

2-[4-(3-Fluoro-phenoxy)-benzyl]-7-methyl-5-pyridin-2-yl-2,3-dihydro-isoindol-1-one

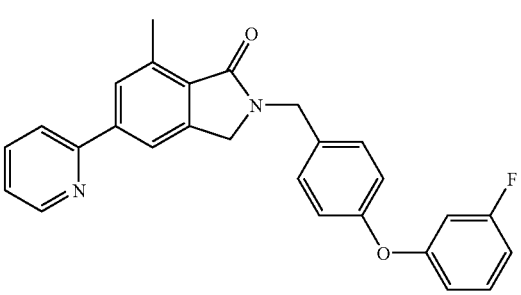

41 mg, 41%, colourless oil. 8.70-8.75 (m, 1H), 7.75-7.88 (m, 4H), 7.25-7.37 (m, 4H), 7.03 (d, 2H), 6.75-6.85 (m, 2H), 6.65-6.73 (m, 1H), 4.81 (s, 2H), 4.14 (s, 2H), 2.86 (s, 3H).

EXAMPLE 14

2-[4-(3-Fluoro-phenoxy)-benzyl]-7-methyl-5-pyrazin-2-yl-2,3-dihydro-isoindol-1-one

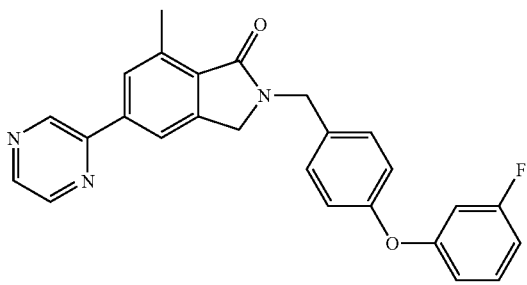

27 mg, 27%, off-white solid. 9.08 (d, 1H), 8.67-8.69 (m, 1H), 8.58 (d, 1H), 7.87-7.89 (m, 2H), 7.35 (d, 2H), 7.27-7.29 (m, 1H), 7.03 (d, 2H), 6.75-6.83 (m, 2H), 6.68-6.72 (m, 1H), 4.81 (s, 2H), 4.36 (s, 2H), 2.88 (s, 3H).

EXAMPLE 15

2-[4-(2-Fluoro-phenoxy)-benzyl]-7-methyl-5-thiazol-2-yl-2,3-dihydro-isoindol-1-one

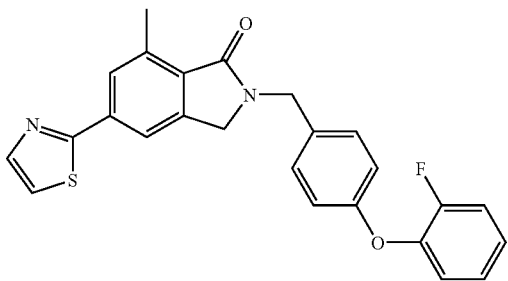

23 mg, 26%, yellow oil. 7.92 (d, 1H), 7.84 (s, 1H), 7.82 (s, 1H), 7.41 (d, 1H), 7.30 (d, 2H), 7.03-7.25 (m, 4H), 6.96 (d, 2H), 4.77 (s, 2H), 4.30 (s, 2H), 2.84 (s, 3H).

What is claimed is:

1. A compound according to formula I:

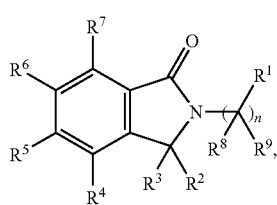

(I)

wherein:

$R^1$ is phenyl optionally substituted by one or more $OC_{1-6}$-alkylhalo groups;

$R^2$ and $R^3$ are independently selected from the group consisting of H and $C_{1-6}$-alkyl;

$R^4$ is H and $R^6$ is selected from the group consisting of H, hydroxy, F, Cl, Br, I, nitro, cyano, $C_{1-6}$-alkyl, and $OC_{1-6}$-alkyl;

$R^5$ is selected from the group consisting of H, F, Cl, Br, I, nitro, CN, $C_{1-6}$-alkyl, $OC_{0-6}$-alkyl, $C_{1-6}$-alkylhalo, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $C_{1-6}$-alkylheteroaryl, $OC_{1-6}$-alkylaryl, $OC_{1-6}$-alkylheteroaryl, $C_{1-6}$-alkylheterocycloalkyl, Oheterocycloalkyl, $OC_{1-6}$-alkylheterocycloalkyl, C(O)H, $(CO)R^{10}$, $O(CO)R^{10}$, $O(CO)OR^{10}$, $C(O)OR^{10}$, $O(CN)OR^{10}$, $C_{1-6}$-alkyl$OR^{10}$, $OC_{2-6}$-alkyl$OR^{10}$, $C_{1-6}$-alkyl$(CO)R^{10}$, $OC_{1-6}$-alkyl$(CO)R^{10}$, $C_{0-6}$-alkyl$CO_2R^{10}$, $C_{1-6}$-alkylcyano, $OC_{2-6}$-alkylcyano, $C_{0-6}$-alkyl$NR^{10}R^{11}$, $OC_{2-6}$-alkyl$NR^{10}R^{11}$, $C_{1-6}$-alkyl$(CO)NR^{10}R^{11}$, $OC_{1-6}$-alkyl$(CO)NR^{10}R^{11}$, $C_{0-6}$-alkyl$NR^{10}(CO)R^{11}$, $OC_{2-6}$-alkyl$NR^{10}(CO)R^{11}$, $C_{0-6}$-alkyl$NR^{10}(CO)NR^{10}R^{11}$, $C_{0-6}$-alkyl$SR^{10}$, $OC_{2-6}$-alkyl$SR^{10}$, $C_{0-6}$-alkyl$(SO)R^{10}$, $OC_{2-6}$-alkyl$(SO)R^{10}$, $C_{0-6}$-alkyl$SO_2R^{10}$, $OC_{2-6}$-alkyl$SO_2R^{10}$, $C_{0-6}$-alkyl$(SO_2)NR^{10}R^{11}$, $OC_{2-6}$-alkyl$(SO_2)NR^{10}R^{11}$, $C_{0-6}$-alkyl$NR^{10}(SO_2)R^{11}$, $OC_{2-6}$-alkyl$NR^{10}(SO_2)R^{11}$, $C_{0-6}$-alkyl$NR^{10}(SO_2)NR^{10}R^{11}$, $OC_{2-6}$-alkyl$NR^{10}(SO_2)NR^{10}R^{11}$, $(CO)NR^{10}R^{11}$, $O(CO)NR^{10}R^{11}$, $NR^{10}OR^{11}$, $C_{0-6}$-alkyl$NR^{10}(CO)OR^{11}$, $OC_{2-6}$-alkyl$NR^{10}(CO)OR^{11}$, $SO_3R^{10}$, and a 5- to 7-membered ring that may contain one or more heteroatoms independently selected from the group consisting of N, O and S, wherein $R^5$ may be substituted by one or more A, and wherein any cyclic moiety is optionally fused to a 5- to 7-membered ring that may contain one or more heteroatoms independently selected from the group consisting of C, N, O and S;

$R^7$ is selected from the group consisting of H, F, Cl, Br, I, nitro, cyano, $OC_{1-4}$-alkyl and $C_{1-6}$-alkyl;

$R^8$ and $R^9$ are independently selected from the group consisting of H, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, and $OC_{2-6}$-alkynyl;

$R^{10}$ and $R^{11}$ are independently selected from the group consisting of H, hydroxy, oxo, F, Cl, Br, I, nitro, cyano, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $C_{0-6}$-alkyl-heterocycloalkyl, $OC_{1-6}$-alkyl-heterocycloalkyl, heteroaryl, and $C_{1-6}$alkylheteroaryl, wherein any cyclic moiety is optionally fused to a 5- to 7-membered ring that may contain one or more heteroatoms independently selected from the group consisting of C, N, O and S and any cyclic moiety is optionally substituted with a substituent selected from alkyl, halo, hydroxyl, Oalkyl, haloalkyl and Ohaloalkyl;

A is selected from the group consisting of H, hydroxy, F, Cl, Br, I, nitro, cyano, oxo, $C_{1-6}$-alkyl, $C_{1-6}$-alkylhalo, $OC_{1-6}$alkyl, $OC_{1-6}$-alkylhalo, $C_{2-6}$-alkenyl, $OC_{2-6}$-alkenyl, $C_{2-6}$-alkynyl, $OC_{2-6}$-alkynyl, $C_{3-8}$-cycloalkyl, $C_{1-6}$-alkyl-$C_{3-8}$-cycloalkyl, $OC_{0-6}$-alkyl-$C_{3-8}$-cycloalkyl, aryl, $C_{1-6}$-alkylaryl, $OC_{0-6}$-alkylaryl, $C_{1-6}$-alkyl-heterocyclyl, $C_{1-6}$-alkyl-heterocycloalkyl, $OC_{0-6}$-alkyl-heterocycloalkyl, $(CO)R^{10}$, $0(CO)R^{10}$, $0(CO)OR^{10}$, $O(CNR^{10})OR^{11}$, $C_{1-6}$-alkyl$OR^{10}$, $OC_{2-6}$-alkyl$OR^{10}$, $C_{1-6}$-alkyl$(CO)R^{10}$, $OC_{1-6}$-alkyl$(CO)R^{10}$, $C_{0-6}$-alkyl$CO_2R^{10}$, $OC_{1-6}$-alkyl$CO_2R^{10}$, $C_{1-6}$-alkylcyano, $OC_{2-6}$-alkylcyano, $C_{0-6}$-alkyl$NR^{10}R^{11}$, $OC_{2-6}$-alkyl$NR^{10}R^{11}$, $C_{0-6}$-alkyl$(CO)NR^{10}R^{11}$, $OC_{1-6}$-alkyl$(CO)NR^{10}R^{11}$, $C_{0-6}$-alkyl$NR^{10}(CO)R^{11}$, $OC_{2-6}$-alkyl$NR^{10}(CO)R^{11}$, $C_{0-6}$-alkyl$NR^{10}(CO)NR^{10}$, $R^{11}$, $C_{0-6}$-alkyl$SR^{10}$, $OC_{2-6}$-alkyl$SR^{10}$, $C_{0-6}$-alkyl$(SO)R^{10}$, $OC_{2-6}$-alkyl$(SO)R^{10}$, $C_{1-6}$-alkyl$SO_2R^{10}$, $OC_{2-6}$- alkylSO₂R¹⁰, C₀₋₆-alkyl(SO₂)NR¹⁰R¹¹, OC₂₋₆-alkyl(SO₂)NR¹⁰R¹¹, C₀₋₆-alkylNR¹⁰(SO₂)R¹¹, OC₂₋₆-alkylNR¹⁰(SO₂)R¹¹, C₀₋₆-alkylNR¹⁰(SO₂)NR¹⁰R¹¹, OC₂₋₆-alkylNR¹⁰(SO₂)NR¹⁰R¹¹, (CO)NR¹⁰R¹¹, O(CO)NR¹⁰R¹¹, NR¹⁰OR¹¹, C₀₋₆-alkylNR¹⁰(CO)OR¹¹, OC₂₋₆-alkylNR¹⁰(CO)OR¹¹, SO₃R¹⁰ and a 5- to 7-membered ring that may contain one or more heteroatoms independently selected from the group consisting of N, O and S, wherein said 5- to 7-membered ring is optionally substituted by one or more of R¹⁰ and R¹¹; and n is 1;

or a pharmaceutically acceptable salt, or optical isomer, or combination of any foregoing compound, pharmaceutically acceptable salt or isomer.

2. A compound according to claim 1, wherein:

R², R³, R⁴, R⁶, R⁸, and R⁹ are each H and n is 1, and

R⁷ is selected from H, Cl, Br, I, C₁₋₆-alkyl, and OC₁₋₄-alkyl;

or a pharmaceutically acceptable salt, or optical isomer, or combination of any foregoing compound, pharmaceutically acceptable salt or isomer.

3. A pharmaceutical composition comprising a compound, a pharmaceutically acceptable salt thereof or an optical isomer thereof according to claim 1 and a pharmaceutically acceptable carrier or excipient.

\* \* \* \* \*